United States Patent [19]

Laney et al.

[11] Patent Number: 5,679,512
[45] Date of Patent: Oct. 21, 1997

[54] METHOD FOR INTRODUCING DEFINED SEQUENCES AT THE 3'END OF POLYNUCLEOTIDES

[75] Inventors: Maureen Laney; Yan Chen, both of Palo Alto; Edwin F. Ullman, Atherton; Karen M. Hahnenberger, Cupertino, all of Calif.

[73] Assignee: Behringwerke AG, Marburg, Germany

[21] Appl. No.: 140,349

[22] Filed: Oct. 20, 1993

Related U.S. Application Data

[63] Continuation-in-part of Ser. No. 923,079, Jul. 31, 1992, abandoned.

[51] Int. Cl.$^6$ .............................. C12Q 1/68; C12P 19/34
[52] U.S. Cl. ................................ 435/6; 435/91.1
[58] Field of Search ..................... 435/91.1, 6; 935/78

[56] References Cited

U.S. PATENT DOCUMENTS

| | | | |
|---|---|---|---|
| 4,358,535 | 11/1982 | Falkow et al. | 435/5 |
| 4,423,153 | 12/1983 | Ranney et al. | 436/63 |
| 4,480,040 | 10/1984 | Owens et al. | 436/504 |
| 4,486,539 | 12/1984 | Ranki et al. | 436/504 |
| 4,490,472 | 12/1984 | Gottlieb | 436/504 |
| 4,599,303 | 7/1986 | Yabusaki et al. | 435/6 |
| 4,647,529 | 3/1987 | Rodland et al. | 435/6 |
| 4,656,134 | 4/1987 | Ringold | 435/91 |
| 4,663,283 | 5/1987 | Kleid et al. | 435/91 |
| 4,675,283 | 6/1987 | Robinson | 435/6 |
| 4,677,054 | 6/1987 | White et al. | 435/6 |
| 4,683,195 | 7/1987 | Mullis et al. | 435/6 |
| 4,683,202 | 7/1987 | Mullis | 435/91 |
| 4,724,202 | 2/1988 | Dattagupta et al. | 435/6 |
| 4,800,159 | 1/1989 | Mullis et al. | 435/6 |
| 4,882,269 | 11/1989 | Schneider et al. | 435/6 |
| 4,908,307 | 3/1990 | Rodland et al. | 435/6 |
| 4,965,188 | 10/1990 | Mullis et al. | 435/6 |
| 5,008,182 | 4/1991 | Sninsky et al. | 435/5 |
| 5,043,272 | 8/1991 | Hartley | 435/91 |
| 5,066,584 | 11/1991 | Gyllensten et al. | 435/91 |

FOREIGN PATENT DOCUMENTS

| | | |
|---|---|---|
| 904402 | 3/1986 | Belgium . |
| 0 164 054 A1 | 12/1985 | European Pat. Off. . |
| 0 185 494 A2 | 6/1986 | European Pat. Off. . |
| 0 194 545 A2 | 9/1986 | European Pat. Off. . |
| 0 200 362 A2 | 12/1986 | European Pat. Off. . |
| 0 302 175 A2 | 2/1989 | European Pat. Off. . |
| 0 318 245 | 5/1989 | European Pat. Off. . |
| 0 379 369 | 7/1990 | European Pat. Off. . |
| 0 469 755 | 2/1992 | European Pat. Off. . |
| 0 552 931 | 7/1993 | European Pat. Off. . |
| WO 89/12695 | 12/1989 | WIPO . |
| WO 93/06240 | 4/1993 | WIPO . |

OTHER PUBLICATIONS

Bischofberger, et al., Nucleic Acids Research, (1987)vol. 15:2 pp. 709–716 "Cleavage of single stranded oligonucleotides by EcoRI restriction endonuclease".

Brigati, et al., Virology, (1983) vol. 126: pp. 32–50 "Detection of Viral Genomes in Cultured Cells and Paraffin–Embedded Tissue Sections Using Biotin–Labeled Hybridization Probes".

Bugawan, et al., Bio/Technology, (Aug. 1988) vol. 6: pp. 943–947 "The use of non–radioactive oligonucleotide probes to analyze enzymatically amplified DNA for prenatal diagnosis and forsensic HLA typing".

de Jong, et al., Publication By Lawrence Livermore Labs, (PCR User Meeting Jan. 16, 1990, San Francisco, CA) "Isolation of Region–Specific Probes by ALU–PCR and Coincidence Cloning".

Fahrlander, et al., Bio/Technology, (Oct. 1988) vol 6: pp. 1165–1168 "Amplifying DNA probe signals: A 'Christmas Tree' Approach".

Frohman, et al., Proc. Natl. Acad. Science USA, (Dec. 1988) vol. 85, pp. 8998–9002 "Rapid production of full–length cDNAs from rare transcripts: Amplification using a single gene–specific oligonucleotide primer".

Goldkorn, et al., Nucleic Acids Research, (1986) vol. 14:22, pp. 9171–9191 "A simple and efficient enzymatic method for covalent attachment of DNA to cellulose. Application for hybridization–restriction analysis and for in vitro synthesis of DNA probes".

Langer, et al., Proc. Natl. Acad. Science USA, (Nov. 1981) vol. 78:11 pp. 6633–6637 "Enzymatic synthesis of biotin–labeled polynucleotides: Novel nucleic acid affinity probes".

Lizardi, et al., Bio/Technology, (Oct. 1988) vol 6: pp. 1197–1202 "Exponential amplification of recombinant–RNA hybridization probes".

Nelson, et al., Proc. Natl. Acad. Science USA, (Sep. 1989) vol. 86: pp. 6686–6690 "Alu Polymerase chain reaction: A method for rapid isolation of human–specific sequences from complex DNA sources".

(List continued on next page.)

Primary Examiner—W. Gary Jones
Assistant Examiner—Eggerton Campbell
Attorney, Agent, or Firm—Theodore J. Leitereg

[57] ABSTRACT

A method is disclosed for extending a primer to produce a single stranded polydeoxynucleotide that has two or more defined sequences. A combination is provided which comprises a template polynucleotide, a blocker polynucleotide, a primer polynucleotide and a polynucleotide Q. The template polynucleotide has three sequences T1, T2 and T3 wherein T1 is non-contiguous and 3' of T3 and wherein the 5' end of T3 is 5' of the 5' end of T2. The primer polynucleotide has a second defined sequence at its 3' end that is hybridizable with T1. The blocker polynucleotide has sequence B1 that is hybridizable with T3. Polynucleotide Q has sequences S1 and S2 wherein S1 is 3' of S2 and homologous with T2 and S2 is complementary to a first defined sequence that is to be introduced at the 3' end of the polynucleotide primer, when it is extended during the method of the invention. Polynucleotide Q is either attached to the 5' end of the blocker polynucleotide or present as a separate reagent. The primer is extended along the template polynucleotide and along at least a portion of sequence T2 and thereafter along the polynucleotide Q to give a single stranded polynucleotide having two or more defined sequences.

39 Claims, 16 Drawing Sheets

OTHER PUBLICATIONS

Paabo, et al., The Journal Of Biological Chemistry, (1990) vol. 265:8 pp. 4718–4721 "DNA Damage Promotes Jumping between Templates during Enzymatic Amplification".

Parks, et al., Nucleic Acids Research, (1991) vol. 19:25 pp. 7155–7160 "A polymerase chain reaction mediated by a single primer: cloning of genomic sequences adjacent to a serotonin receptor protein coding region".

Saiki, et al. Science, (Dec. 1985) vol. 230: pp. 1350–1354 "Enzymatic Amplification of β–Globin Genomic Sequences and Restriction Site Analysis for Diagnosis of Sickle Cell Anemia".

Saiki, et al. Science, (Jan. 1988) vol. 239 pp. 487–491 "Primer–Directed Enzymatic Amplification of DNA with a Thermostable DNA Polymerase".

Strobel, et al., Molecular And Cellular Biology, (Jul. 1986) vol. 6:7 pp. 2674–2683 "Intron Mutations Affect Splicing of *Saccharomyces cerevisiae* SUP53 Precursor tRNA".

Stoflet, et al., Science, (Jan. 1988) vol. 239 pp. 491–494 "Genomic Amplification with Transcript Sequencing".

Timblin, et al., Nucleic Acids Research, (1990) vol. 18:6, pp. 1587–1593 "Application for PCR technology to subtractive cDNA cloning: Identificatin of genes expressed specifically in murine plasmacytoma cells".

Wang, et al., DNA And Cell Biology, (1991) vol. 10:10 pp. 771–777 "Single Primer–Mediated Polymerase Chain Reaction: Application in Cloning of Two Different 5'–Untranslated Sequences of Acidic Fibroblast Growth Factor mRNA".

Watson, et al., Molecular Biology Of The Gene, Fourth Edition, The Benjamin/Cummings Publishing Co. Inc., Menlo Park, CA pp. 939–941 "Reverse Transcriptase Generates Long Terminal Repeats in Proviral DNA".

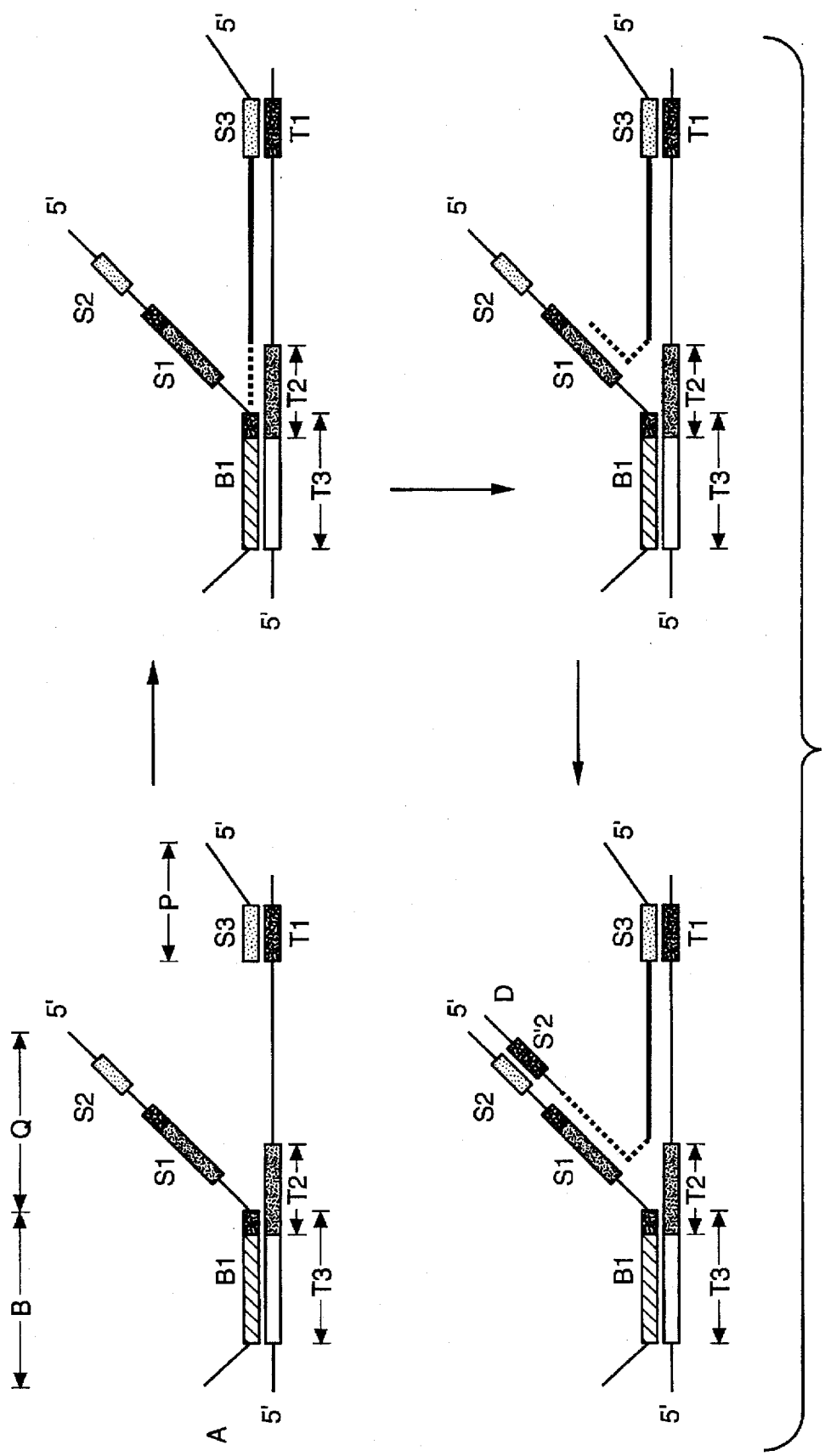
FIG._1

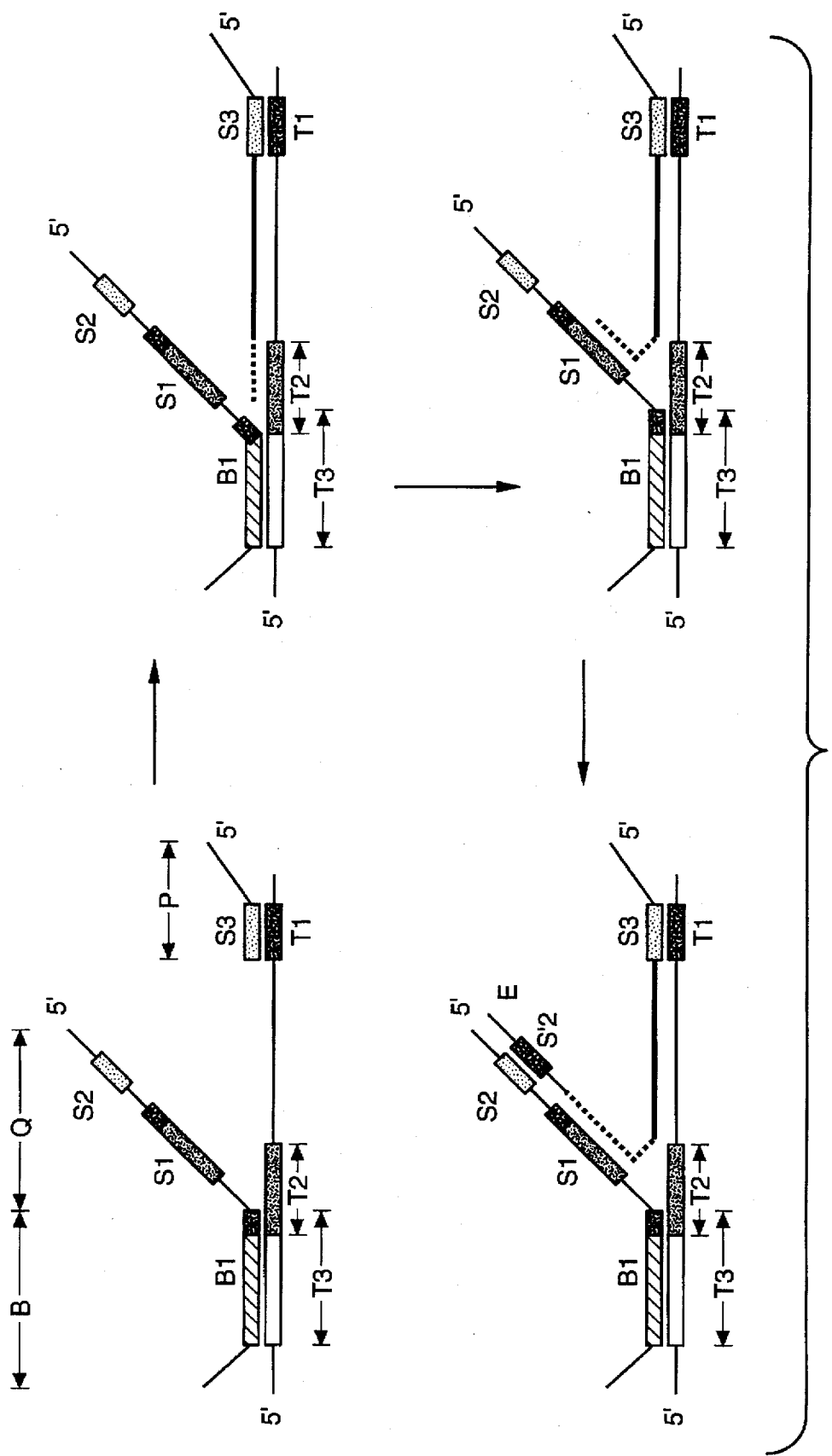
FIG._2

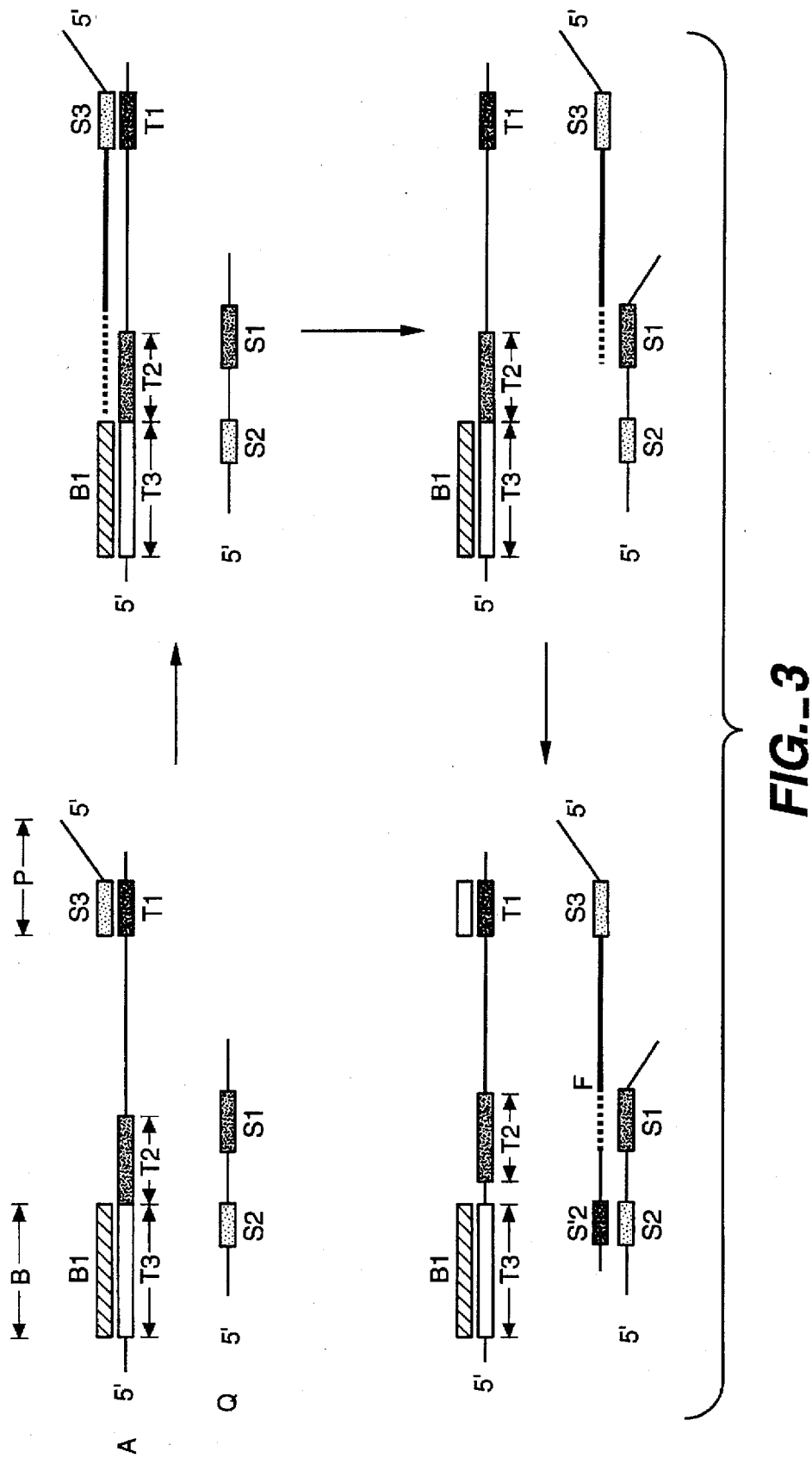
FIG._3

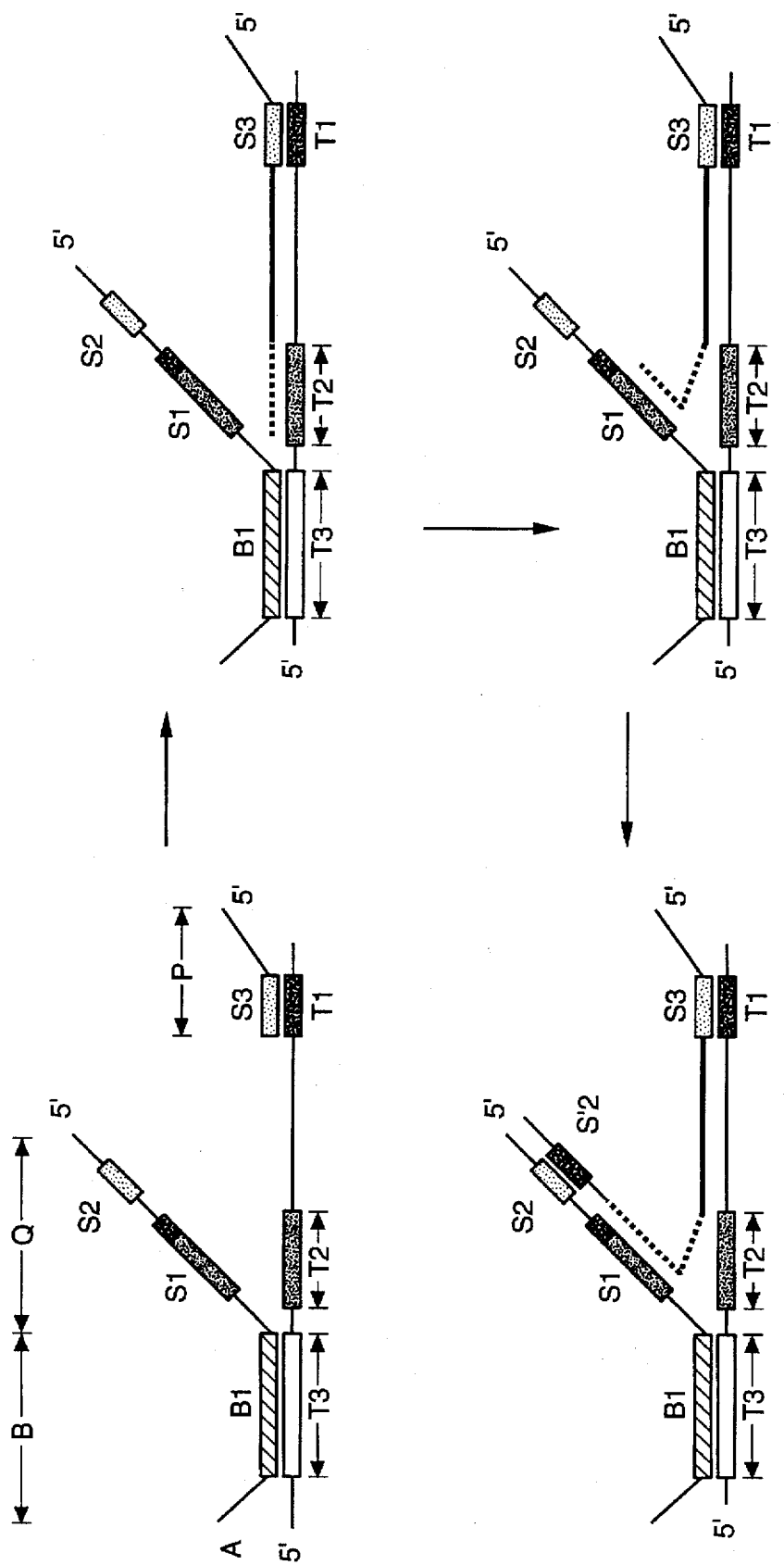
FIG._4

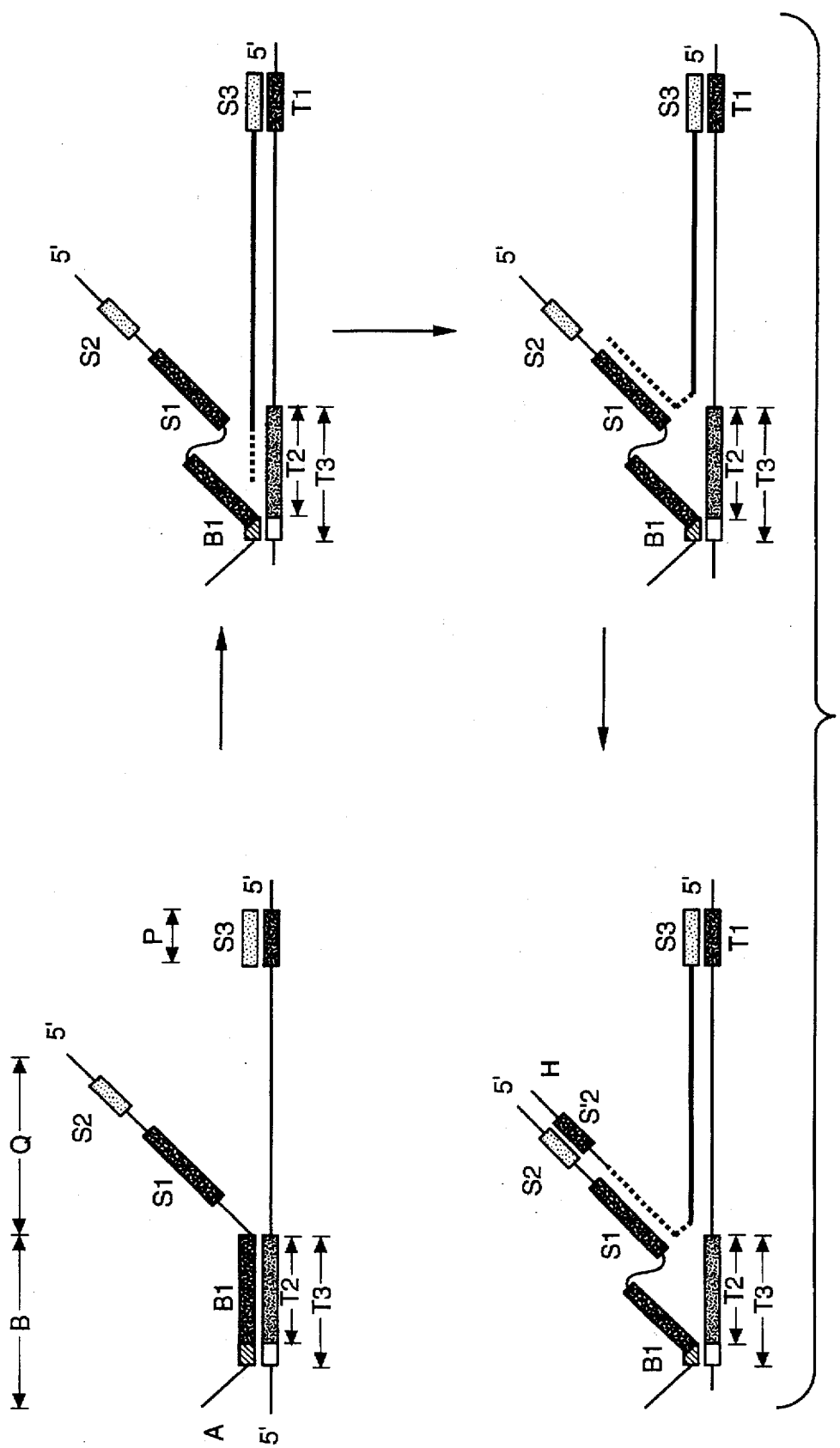
FIG._5

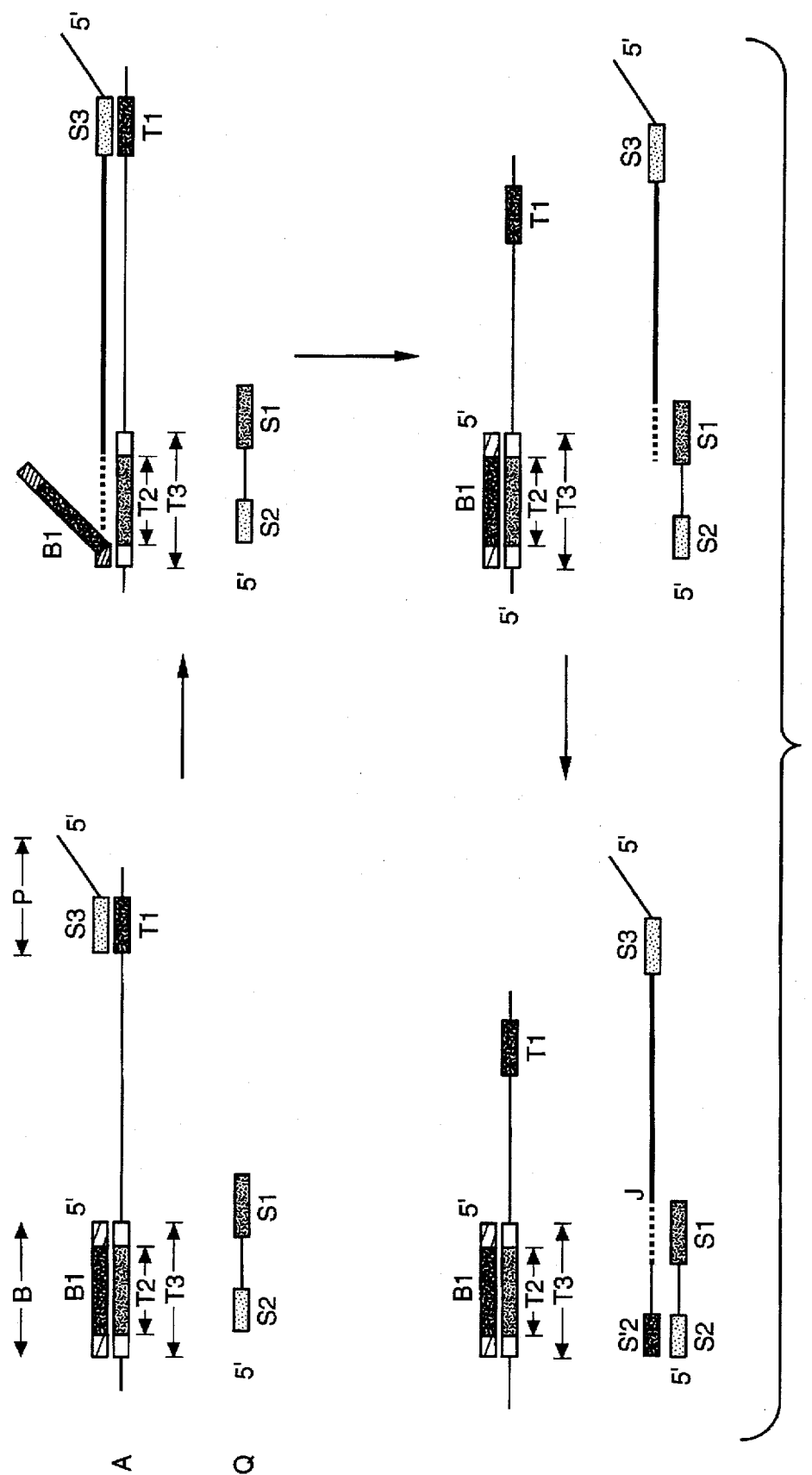
FIG._6

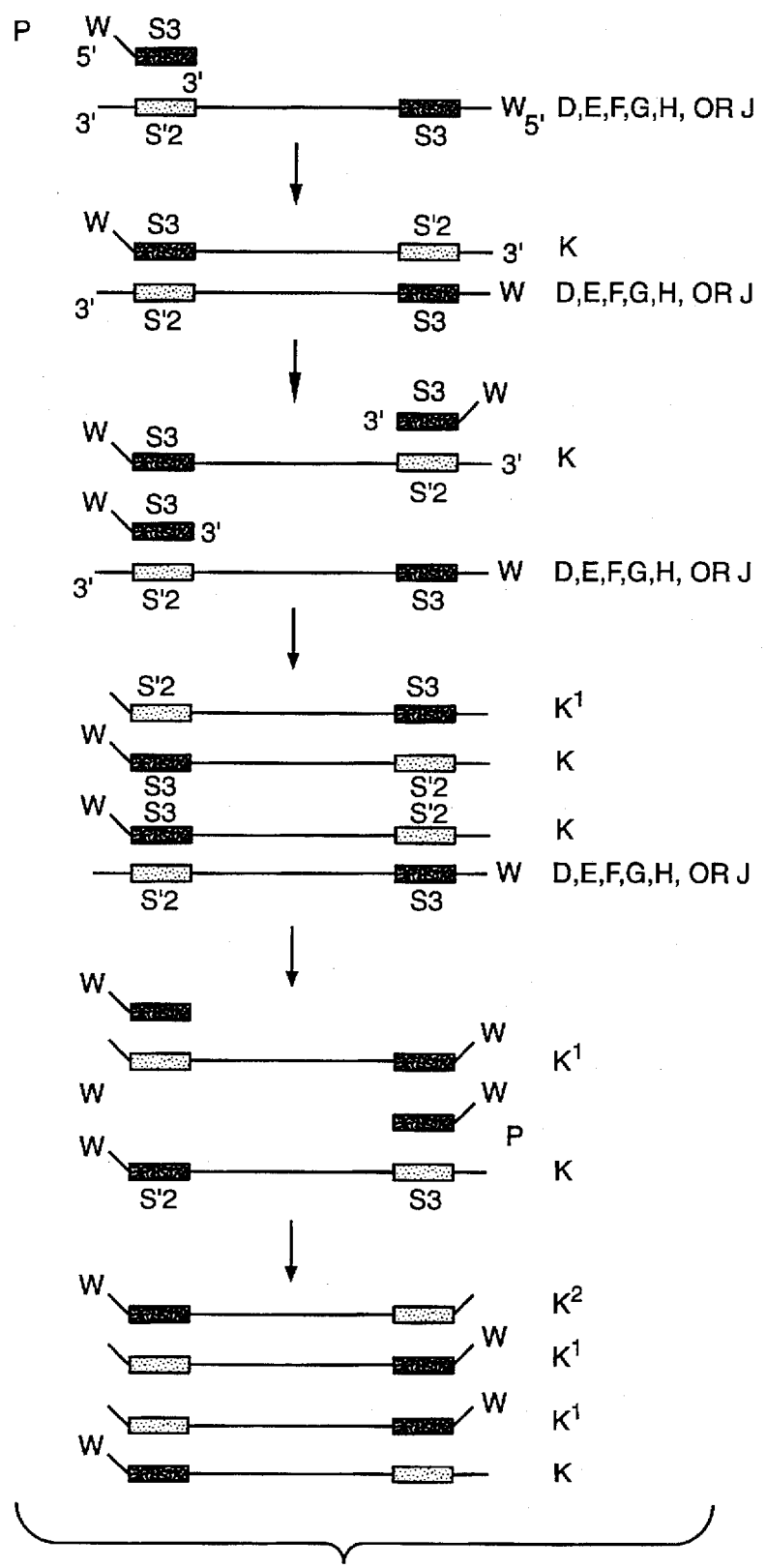
FIG._7

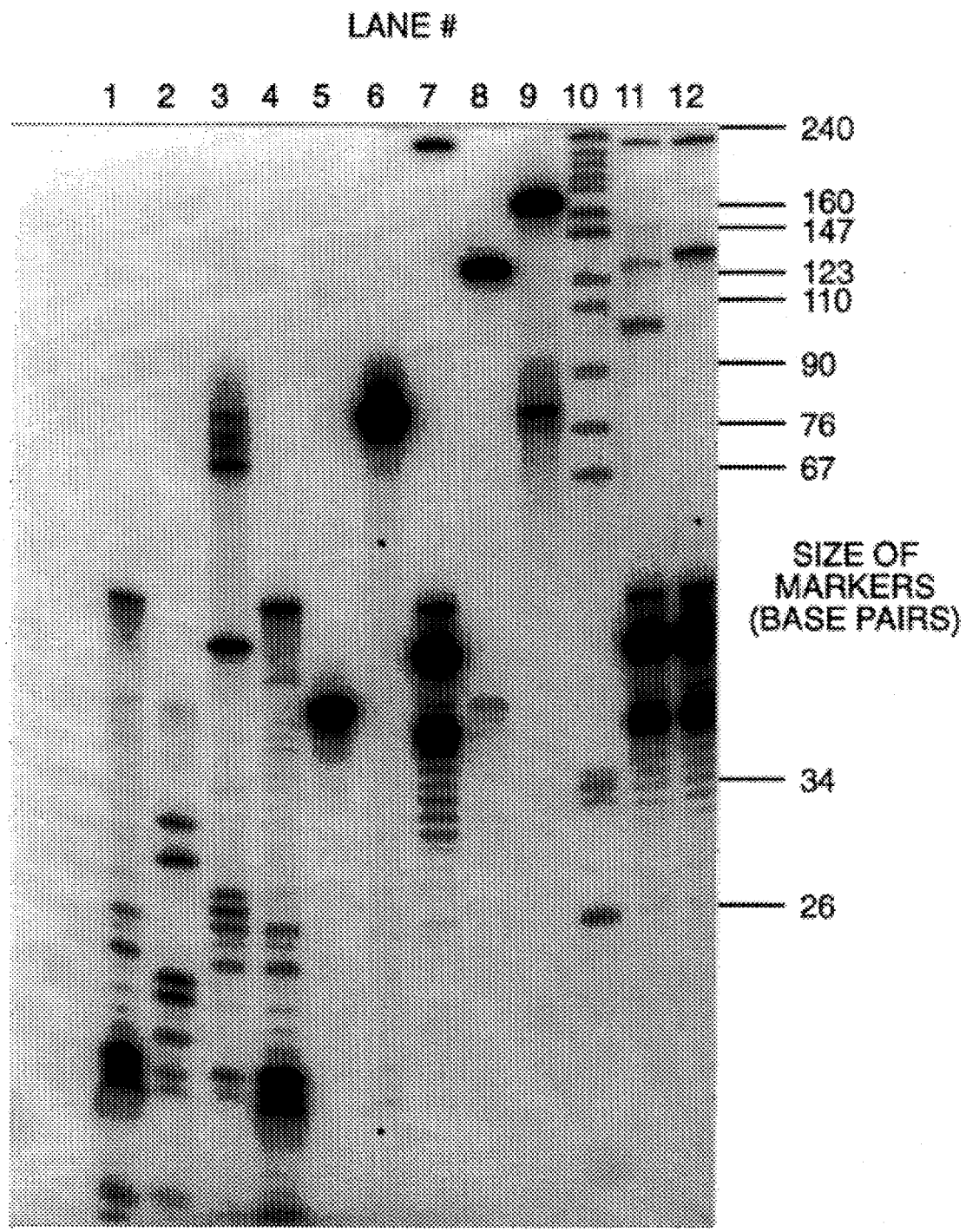
FIG._8

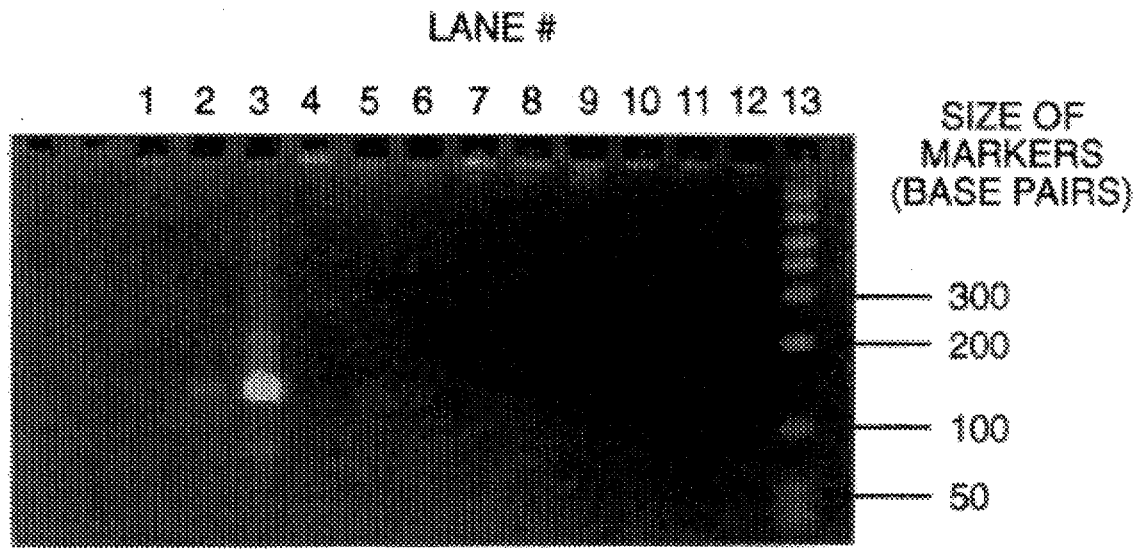
FIG._9A
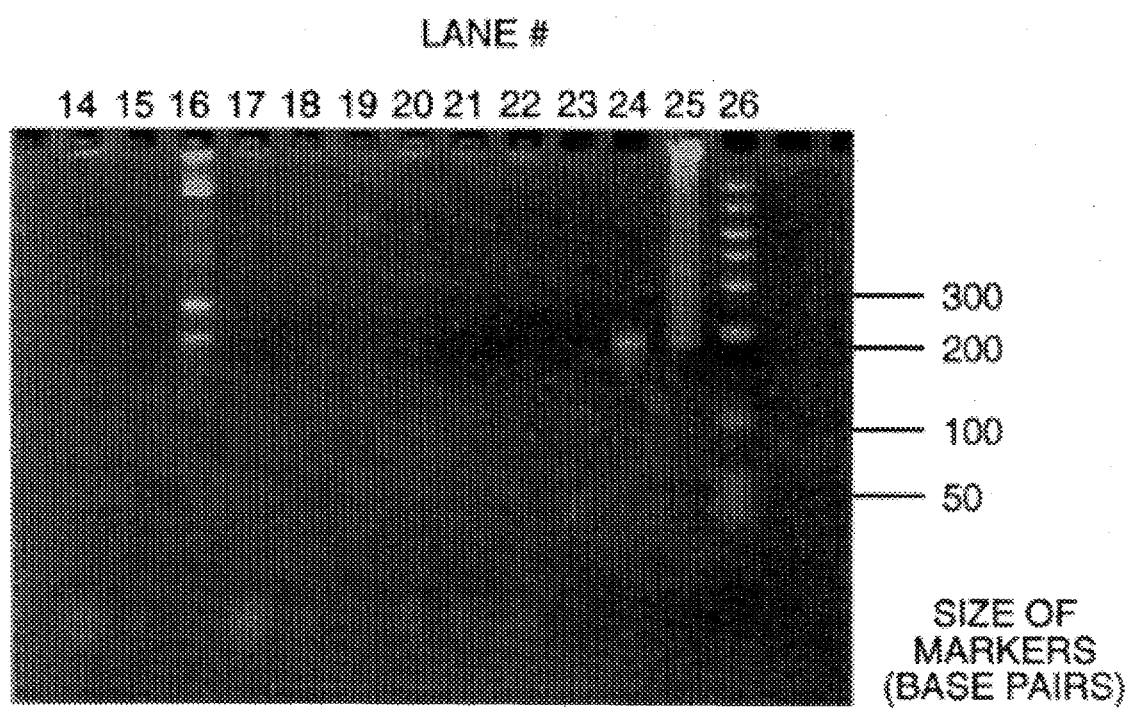
FIG._9B

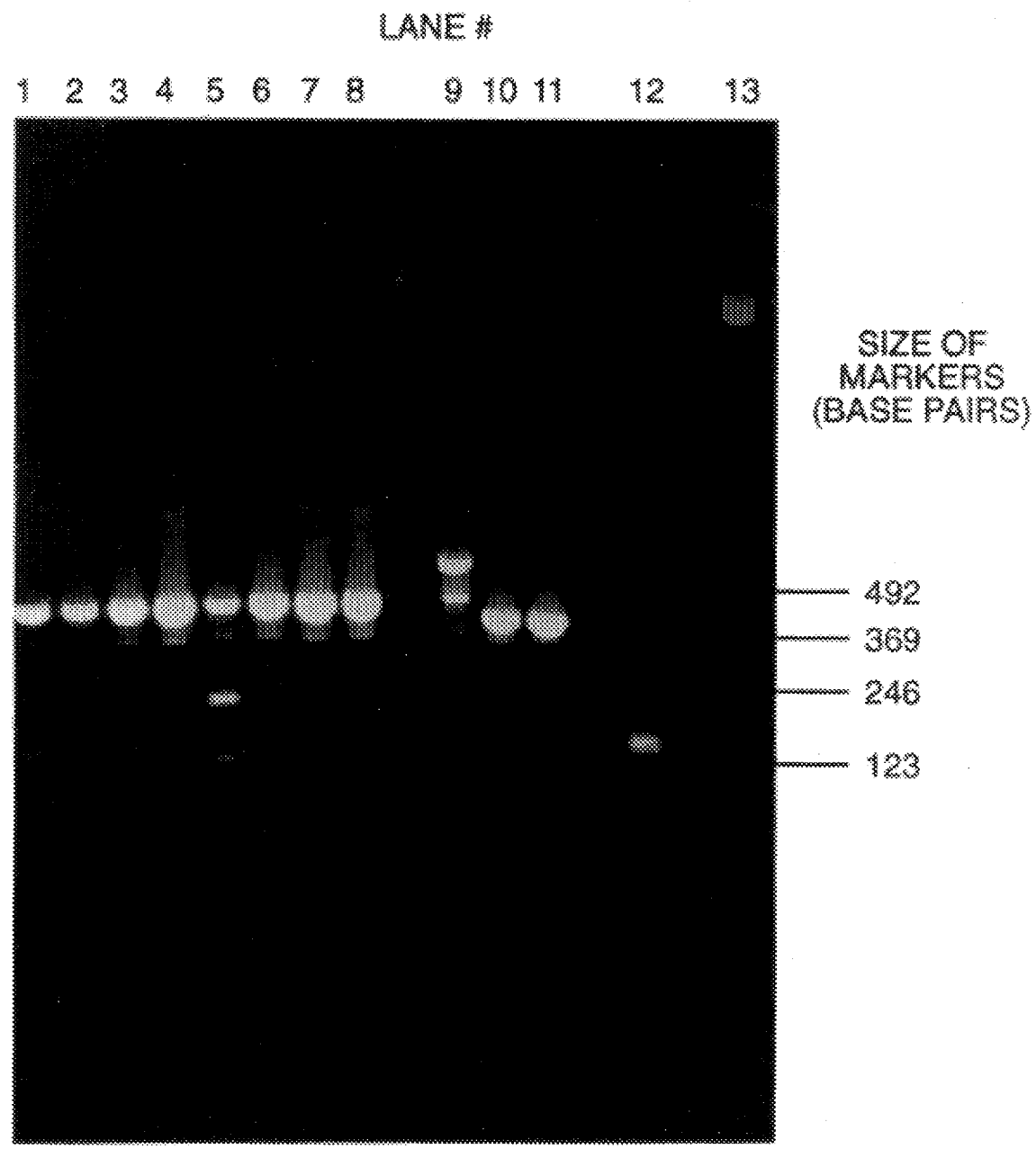
FIG._10

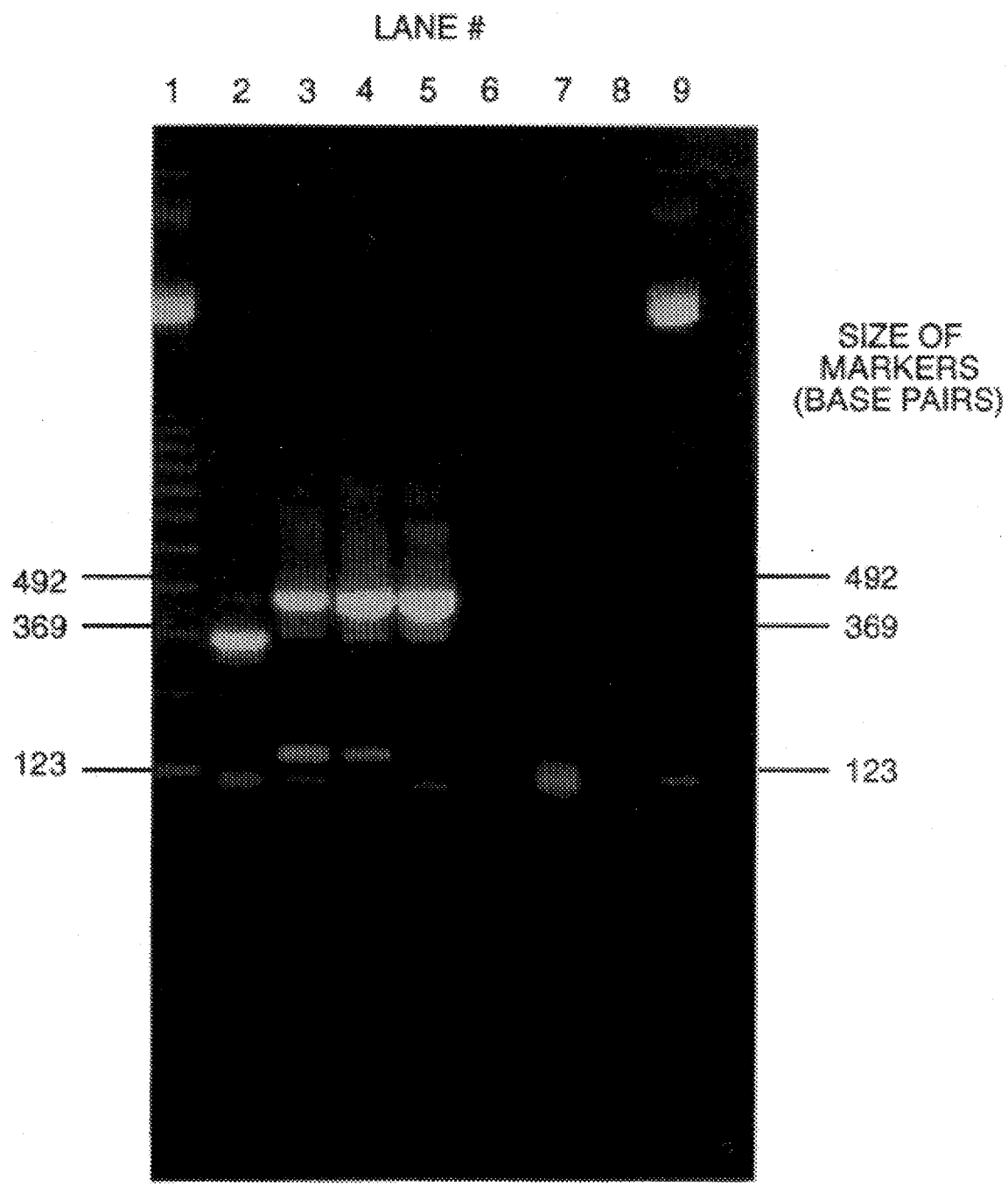
FIG._11

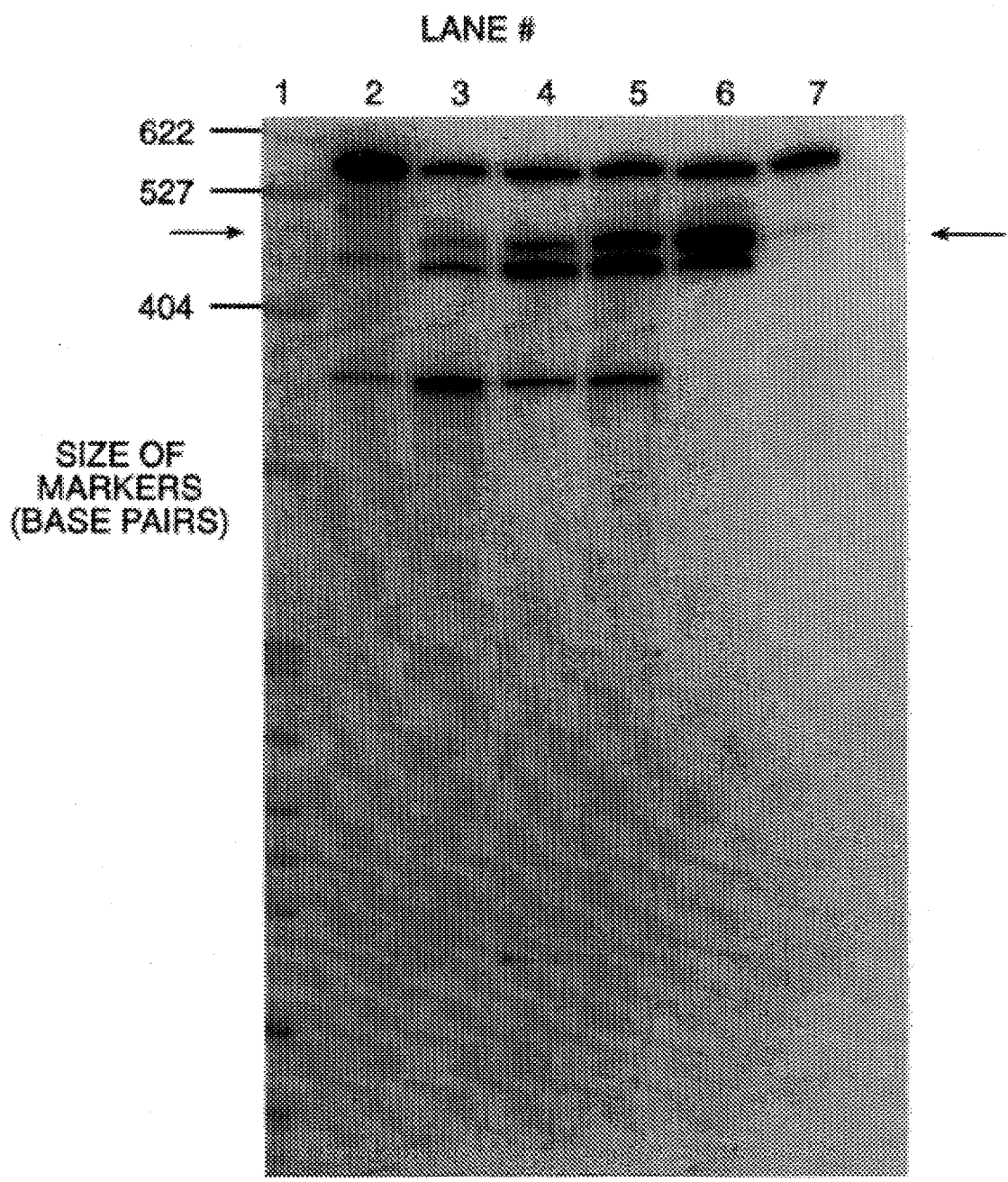
FIG._12

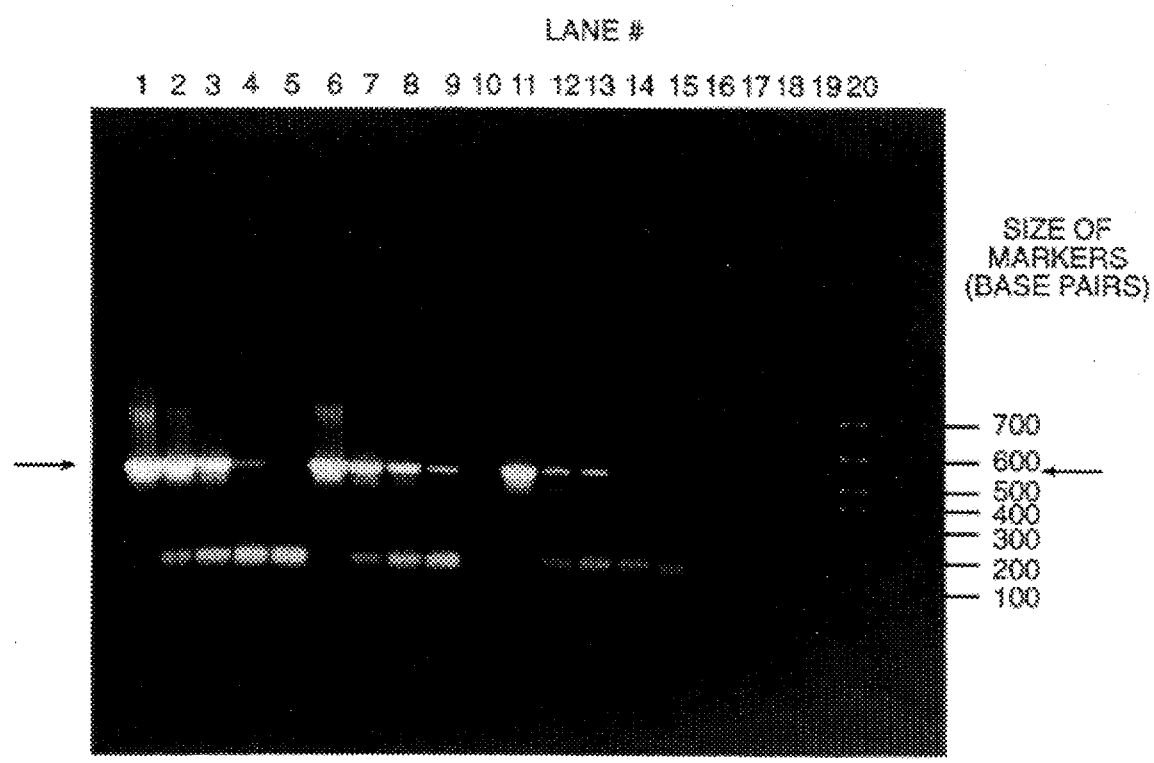
FIG._13

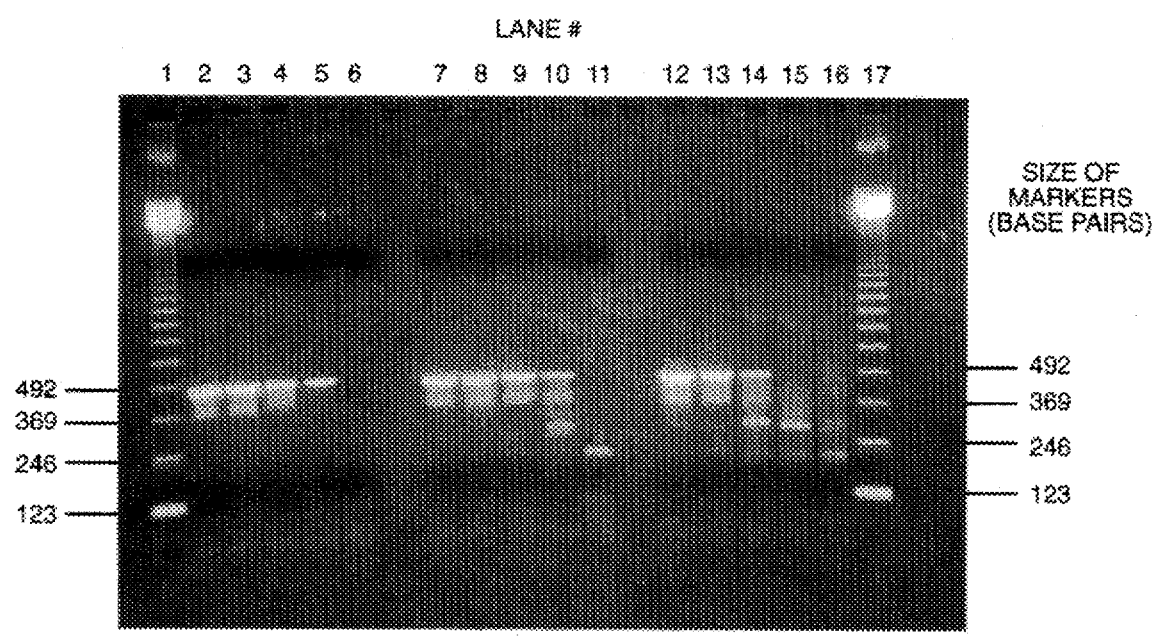
FIG._14

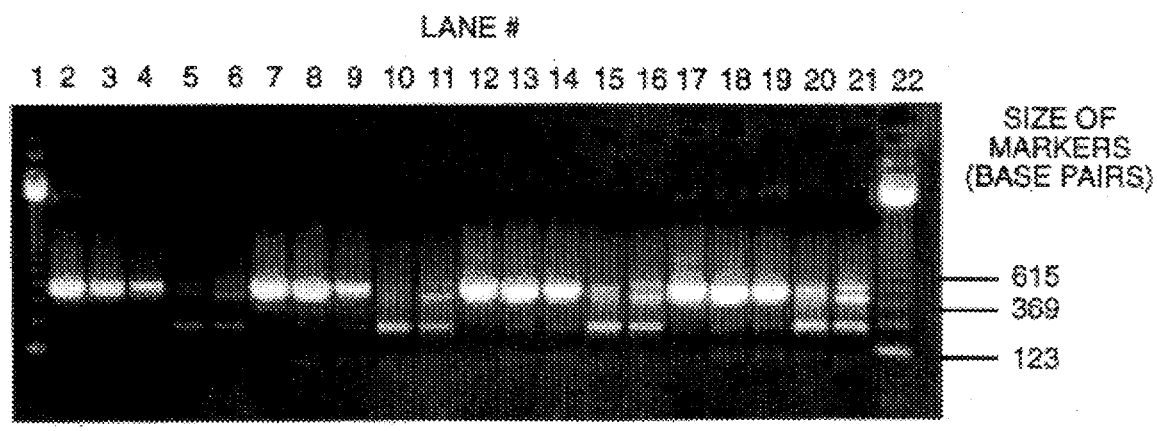
FIG._15

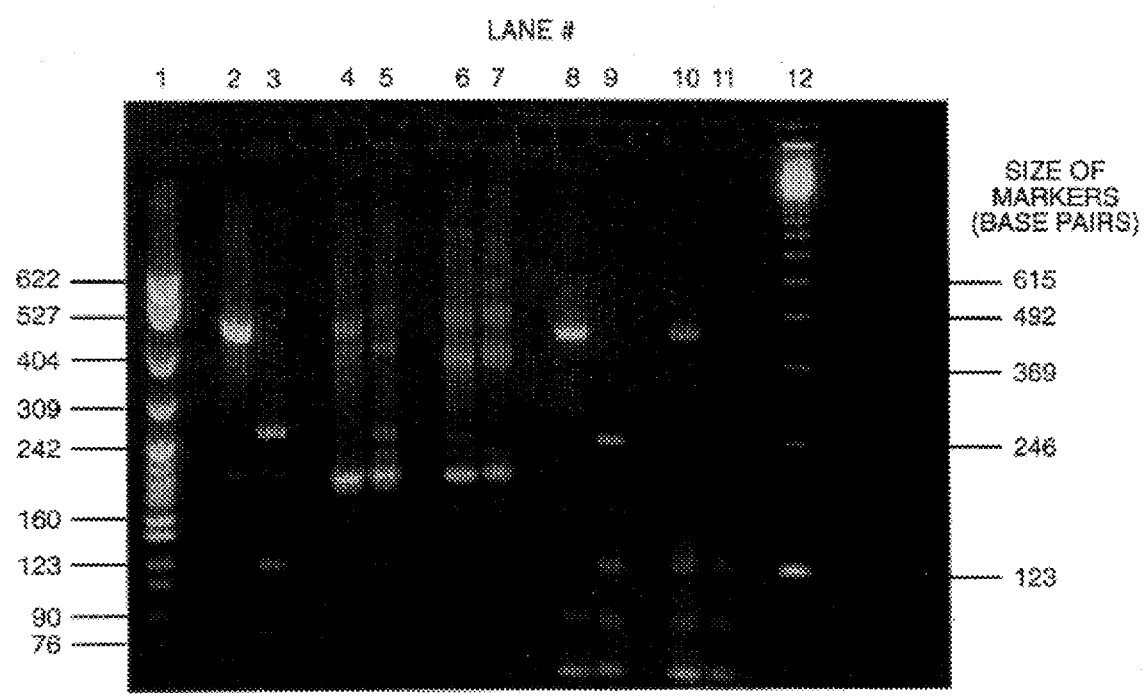
FIG._16

METHOD FOR INTRODUCING DEFINED SEQUENCES AT THE 3'END OF POLYNUCLEOTIDES

CROSS-REFERENCE TO RELATED APPLICATIONS

This application is a continuation-in-part of U.S. patent application Ser. No. 07/923,079 filed Jul. 31, 1992, abandoned the disclosure of which is incorporated herein by reference in its entirety.

BACKGROUND OF THE INVENTION

1. Field of the InventiOn.

Nucleic acid hybridization has been employed for investigating the identity and establishing the presence of nucleic acids. Hybridization is based on complementary base pairing. When complementary single stranded nucleic acids are incubated together, the complementary base sequences pair to form double stranded hybrid molecules. The ability of single stranded deoxyribonucleic acid (ssDNA) or ribonucleic acid (RNA) to form a hydrogen bonded structure with a complementary nucleic acid sequence has been employed as an analytical tool in molecular biology research. The availability of radioactive nucleoside triphosphates of high specific activity and the $^{32}P$ labelling of DNA with T4 kinase has made it possible to identify, isolate, and characterize various nucleic acid sequences of biological interest. Nucleic acid hybridization has great potential in diagnosing disease states associated with unique nucleic acid sequences. These unique nucleic acid sequences may result from genetic or environmental change in DNA by insertions, deletions, point mutations, or by acquiring foreign DNA or RNA by means of infection by bacteria, molds, fungi, and viruses. Nucleic acid hybridization has, until now, been employed primarily in academic and industrial molecular biology laboratories. The application of nucleic acid hybridization as a diagnostic tool in clinical medicine is limited because of the frequently very low concentrations of disease related DNA or RNA present in a patient's body fluid and the unavailability of a sufficiently sensitive method of nucleic acid hybridization analysis.

Commonly used methods for detecting specific nucleic acid sequences generally involve immobilization of the target nucleic acid on a solid support such as nitrocellulose paper, cellulose paper, diazotized paper, or a nylon membrane. After the target nucleic acid is fixed on the support, the support is contacted with a suitably labelled probe nucleic acid for about two to forty-eight hours. After the above time period, the solid support is washed several times at a controlled temperature to remove unhybridized probe. The presence of hybridized material on the support is detected by autoradiography or by spectrometric methods.

Since these methods are slow and labor intensive, and generally not suitable for very low concentrations, it is desirable to develop methods with increased sensitivity and simplicity. Preferably, new methods should avoid the hazards of radioactivity and employ homogeneous assay techniques, which offer opportunities for speed and simplicity.

Recently, a method for the enzymatic amplification of specific double stranded sequences of DNA known as the polymerase chain reaction (PCR) has been described. This in vitro amplification procedure is based on repeated cycles of denaturation, oligonucleotide primer annealing, and primer extension by thermophilic polymerase, resulting in the exponential increase in copies of the desired sequence flanked by the primers. The PCR primers, which anneal to opposite strands of the DNA, are positioned so that the polymerase catalyzed extension product of one primer can serve as a template strand for the other, leading to the accumulation of a discrete double stranded fragment whose length is defined by the distance between the 5' ends of the oligonucleotide primers.

2. Description Of the Related Art

Paabo, et al., discuss jumping between templates during enzymatic amplification promoted by DNA damage (*J. Biol. Chem.* (1990) 265(No.8): 4718–4721).

U.S. patent applications Ser. Nos. 07/299,282 and 07/399,795, filed Jan. 19, 1989, and Aug. 29, 1989, respectively, describe nucleic acid amplification using a single polynucleotide primer. U.S. patent application Ser. No. 07/555,323 filed Jul. 19, 1990, discloses methods for producing a polynucleotide for use in single primer amplification. U.S. patent application Ser. No. 07/555,968 describes a method for producing a molecule containing an intramolecular base-pair structure. The disclosures of these four applications are incorporated herein by reference in their entirety.

A process for amplifying, detecting and/or cloning nucleic acid sequences otherwise referred to as PCR is disclosed in U.S. Pat. Nos. 5,008,182, 4,965,188, 4,800,159, 4,683,195 and 4,683,202. Sequence polymerization by PCR is described by Saiki, et al., (1986) *Science*, 230:1350–1354.

A PCR mediated by a single primer: cloning of genomic sequences adjacent to a serotonin receptor protein coding region is described by Parks, et al., *Nucleic Acids Research* (1991) 19(No.25): 7155–7160. Wang, et al., *DNA and Cell Biology* (1991) 10(No.10): 771–777 discuss the single primer-mediated PCR: application in cloning of two different 5'-untranslated sequences of acidic fibroblast growth factor mRNA.

Rapid production of full-length cDNAs from rare transcripts: amplification using a single gene-specific oligonucleotide primer is discussed by Frohman, et al., in *Proc. Natl. Acad. Sci. USA* (1988) 85:8998–9002. A discussion of the generation of long terminal repeats in proviral DNA by reverse transcriptase is found in "Molecular Biology of the Gene," Fourth Edition, The Benjamin/Cummings Publishing Company, Inc., Menlo Park, Calif., pages 939–941. The effect of intron mutations on the splicing of *Saccharomyces cerevisiae* SUP53 precursor tRNA is discussed by Strobel, et al., in *Molecular and Cellular Biology* (1986) 6(No.7): 2674–2683. Amplification of nucleic acid sequences using oligonucleotides of random sequence as primers is described in U.S. Pat. No. 5,043,272.

A single stranded self-hybridizing nucleic acid probe capable of repeatedly hybridizing to itself or other nucleic acids to forman amplified entity is described in U.S. patent application Ser. No. 06/888,058, filed Jul. 22, 1986. Methods of generating single stranded DNA by PCR are disclosed in U.S. Pat. No. 5,066,584. A method of making an oligonucleotide is described in European Patent Application No. 0 194 545 A2. Belgian patent application No. BE 904,402 discloses a mold for making DNA detection probes. Gene amplification in eukaryotic cells is disclosed in U.S. Pat. No. 4,656,134.

Langer, et al., *Proc. Natl. Acad. Sci. USA*, (1981) 78:6633–6637 discloses the enzymatic synthesis of biotin labelled polynucleotides and the use of these materials as novel nucleic acid affinity probes. The detection of viral genomes in cultured cells and paraffin imbedded tissue sections using biotin labelled hybridization probes is discussed by Brigati, et al., *Virology*, (1983) 126:32–50. U.S.

Pat. No. 4,486,539 discloses the detection of microbial nucleic acids by a one step sandwich hybridization test. Sensitive tests for malignancies based on DNA detection is described in U.S. Pat. No. 4,490,472. U.S. Pat. No. 4,480,040 discloses the sensitive and rapid diagnosis of plant viroid diseases and viruses employing radioactively labelled DNA that is complementary to the viroid or to the nucleic acid of the virus being diagnosed. European patent application 0 302 175 A2 (Priority U.S. patent application 391,440 filed Jun. 23, 1982) teaches modified labelled nucleotides and polynucleotides and methods of preparing, utilizing, and detecting the same. Methods and compositions for the detection and determination of cellular DNA are disclosed in U.S. Pat. No. 4,423,153. Specific DNA probes in diagnostic microbiology are discussed in U.S. Pat. No. 4,358,535. A method for detection of polymorphic restriction sites and nucleic acid sequences is discussed in European patent application No. 0 164 054 A1. U.S. Pat. No. 4,663,283 describes a method of altering double-stranded DNA.

Genomic amplification with transcript sequencing is discussed by Stoflet, et al., *Science* (198) 239:491. Primer-directed enzymatic amplification of DNA with a thermostable DNA polymerase is described by Saiki, et al., *Science* (1988) 239:487. U.S. Pat. No. 4,724,202 discloses the use of non-hybridizable nucleic acids for the detection of nucleic acid hybridization. Bugawan, et al., describe the use of non-radioactive oligonucleotide probes to analyze enzymatically amplified DNA for prenatal diagnosis and forensic HLA typing.

Detection and isolation of homologous, repeated and amplified nucleic acid sequences is disclosed in U.S. Pat. No. 4,675,283. European patent application No. 0 200 362 A2 describes a process for amplifying, detecting or cloning nucleic acid sequences and useful in disease diagnosis and in preparation of transformation vectors. A method for simple analysis of relative nucleic acid levels in multiple small samples by cytoplasmic dot hybridization is described in U.S. Pat. No. 4,677,054. A hybridization method of detecting nucleic acid sequences with a probe containing a thionucleotide is described in U.S. Pat. No. 4,647,529.

A simple and efficient enzymatic method for covalent attachment of DNA to cellulose and its application for hybridization-restriction analysis and for in vitro synthesis of DNA probes is described in *Nucleic Acids Research* (1986) 14:9171–9191. Cleavage of single stranded oligonucleotides by Eco RI restriction endonuclease is described in *Nucleic Acid Research* (1987) 15:709–716.

Exponential Amplification of Recombinant-RNA Hybridization Probes is described by Lizardi, et al. (1988) *Bio/Technology* 6:1197–1202. Fahrlander, et al., discusses Amplifying DNA Probe Signals: A Christmas Tree Approach in *Bio/Technology* (1988) 6:1165–1168. A nucleic acid hybridization assay employing probes cross-linkable to target sequences is described in U.S. Pat. No. 4,599,303.

A hybridization method and probe for detecting nucleic acid sequences is described in U.S. Pat. No. 4,908,307. An amplified hybridization assay is described in U.S. Pat. No. 4,882,269 wherein a family of signal-generating secondary probes bind to a primary probe that hybridizes to the target sequence of interest.

Detection of target sequences in nucleic acids by hybridization using diagnostic and contiguous probes for diagnosis of genetic abnormality diseases, especially in an automated procedure, is described in European Patent Application No. 0 185 494 A2.

International patent application No. PCT/US89/02646 describes DNA amplification and subtraction techniques. Timblin, et al., discuss the application of PCR technology to subtractive DNA cloning and the identification of genes expressed specifically in murine plasmacytoma cells in *Nucleic Acids Research* (1990) 18(No.6): 1587–1593. Nelson, et al., disclose Alu PCR as a method for rapid isolation of human-specific sequences from complex DNA sources in *Proc. Natl. Acad. Sci. USA* (1989) 86: 6686–6690. The isolation of region-specific probes by Alu-PCR and coincidence cloning is discussed by de Jong, et al., in a publication of Lawrence Livermore Labs (1990).

SUMMARY OF THE INVENTION

In one embodiment of the present invention a method is described for forming from a primer and a single stranded template polynucleotide a single stranded polydeoxynucleotide having two or more defined sequences. The method comprises: (a) hybridizing a sequence B1 of a blocker polynucleotide to a complementary sequence T3 within a template polynucleotide ("template"), wherein the 5' end of T3 is 5' of the 5' end of a sequence T2, T2 and T3 being 5' to and non-contiguous with a sequence T1 of the template, (b) hybridizing the 3' end of a polynucleotide primer, comprising a second defined sequence, to T1 wherein step (b) is performed prior to, after, or simultaneously with step (a), and (c) extending the primer along the template and along at least a portion of T2. Thereafter, the primer extends along a polynucleotide Q having sequences S1 and S2 wherein S1 is 3' of S2 and homologous with T2. An extended primer is obtained having a first defined nucleic acid sequence at its 3' end that is complementary to S2. Polynucleotide Q is either attached to the 5' end of the blocker polynucleotide or is present as a separate reagent.

In another embodiment of a method in accordance with the invention, a single stranded polydeoxynucleotide having two segments that are non-contiguous and complementary with each other is produced. A combination is formed comprising (a) a template polynucleotide having three sequences T1, T2 and T3 wherein T1 is non-contiguous and 3' of T2 and T3, and the 3' end of T3 is contiguous with or lies within T2, (b) a primer polynucleotide whose 3' end is hybridizable with T1, (c) a blocker polynucleotide with sequence B1, that is hybridizable with sequence T3, and (d) a polynucleotide Q having sequence S1 and S2. Polynucleotide Q is either attached to the 5' end of (in other words is a part of) the blocker polynucleotide or present as a separate reagent. S1 is 3' of S2 and homologous to T2 and S2 is a sequence that is homologous to at least the 3' end of primer polynucleotide. The primer is extended along the template polynucleotide and along at least a portion of T2 and thereafter along polynucleotide Q. The method finds particular application, for example, in single primer amplification assays.

Another embodiment of the invention is a method for forming multiple copies of a target polynucleotide. The method comprises: (a) combining in a medium a template polynucleotide having three sequences T1, T2 and T3 wherein T1 is non-contiguous and 3' of T2 and T3 and wherein the 3' end of T3 is contiguous with or lies within T2 and wherein the target sequence is located between T1 and T3, (2) a primer polynucleotide whose 3' end is hybridizable with T1, (3) a blocker polynucleotide with sequence B1, wherein B1 is hybridizable with T3, (4) a polynucleotide Q having sequences S1 and S2 wherein Q is either attached to the 5' end of the blocker polynucleotide or present as a separate reagent and wherein S1 is 3' of S2 and homologous to T2 and wherein S2 is a sequence that is homologous to at least the 3' end of the primer polynucleotide, (5) DNA polymerase and (6) deoxynucleoside triphosphates under conditions wherein: (A) the blocker becomes hybridized to the sequence T3 of the template polynucleotide, (B) the primer becomes hybridized to the sequence T1 and is extended along the target sequence of the template polynucleotide and along at least a portion of T2 and thereafter along polynucleotide Q to form a duplex, (C) the extended primer is dissociated from the duplex, and (D) the primer hybridizes with and is extended along the extended primer to form a duplex comprising extended primer containing a copy of the target sequence and steps (C) and (D) are repeated.

In another embodiment the presence of a polynucleotide analyte, comprising a template sequence, in a medium suspected of containing the polynucleotide analyte is detected. The template sequence has three sequences T1, T2 and T3 wherein T1 is non-contiguous with and 3' of T2 and T3 and wherein the 5' end of T3 is 5' of the 5' end of T2. The medium is combined with (1) a primer polynucleotide whose 3' end is hybridizable with T1, (2) a blocker polynucleotide with sequence B1, wherein B1 is hybridizable with T3, (3) a polynucleotide Q having sequences S1 and S2 wherein Q is attached to the 5' end of the blocker polynucleotide or is present as a separate reagent and wherein S1 is 3' of S2 and is homologous to T2 and wherein S2 is homologous to at least the 3' end of the primer polynucleotide, (4) DNA polymerase and (5) deoxynucleoside triphosphates. Conditions are chosen wherein: (A) the blocker becomes hybridized to the template sequence, (B) the primer becomes hybridized with and is extended along the template sequence and along at least a portion of T2 and thereafter along polynucleotide Q to form a duplex, (C) the extended primer is dissociated from the duplex, and (D) the primer hybridizes with and is extended along the extended primer to form a duplex comprising extended primer and steps (C) and (D) are repeated. An examination is then carried out for the presence of the extended primer whose presence is determinative of the presence of the polynucleotide analyte. Alternatively, in the above embodiment T1 is non-contiguous with and 3' of T2 and T3 and the 3' end of T3 is contiguous with or lies within T2.

Another embodiment of the present invention concerns a method for producing from a primer polynucleotide a single stranded polydeoxynucleotide having two segments that are non-contiguous and complementary with each other. The method comprises the steps of: (a) providing in combination (1) a template polynucleotide having three sequences T1, T2 and T3 wherein T1 is non-contiguous and 3' of T2 and T3 and the 3' end of T3 is contiguous with or lies within T2 and T2 is comprised of a restriction site at the 5' end of the region homologous to S1 of a polynucleotide Q, (2) a polynucleotide primer whose 3' end is hybridizable with T1, (3) a blocker polynucleotide with sequence B1, wherein B1 is hybridizable with T3, and (4) polynucleotide Q having sequence S1 and sequence S2 wherein Q is either attached to the 5' end of the blocker polynucleotide or present as a separate reagent and wherein S1 is 3' of S2 and homologous to T2 and wherein S2 is a sequence that is homologous to at least the 3' end of the primer polynucleotide, and (b) subjecting the combination to conditions for extending the primer along the template polynucleotide and along at least a portion of T2, cutting the template polynucleotide at the restriction site, hybridizing the partially extended primer to S1 and extending the primer along polynucleotide Q.

Another embodiment of the present invention concerns a method for producing from a polynucleotide primer a single stranded polydeoxynucleotide having two different defined sequences P1 and P'2. In one embodiment the single stranded polydeoxynucleotide is capable of being amplified by the polymerase chain reaction. The method comprises the steps of: (a) providing in combination (1) a template polynucleotide (template) having three sequences T1, T2 and T3 wherein T1 is non-contiguous with and 3' of T2 and T3 and the 3' end of T3 is contiguous with or lies within T2, (2) a polynucleotide primer P1 whose 3' end is hybridizable with T1, (3) a blocker polynucleotide with sequence B1, wherein B1 is hybridizable with T3, and (4) polynucleotide Q having sequences S1 and S2, wherein Q is either attached to the 5' end of the blocker polynucleotide or present as a separate reagent and wherein S1 is 3' of S2 and homologous to T2 and wherein S2 is complementary to P2, and (b) subjecting the combination to conditions for extending the primer P1 along the template and along at least a portion of T2 and thereafter along polynucleotide Q. A second single stranded polydeoxynucleotide is formed by hybridizing a polydeoxynucleotide primer P2 to sequence P'2 of the extended primer disassociated from its duplex and extending P2 along the first extended primer and dissociating the second extended primer from its duplex. The second extended primer is characterized by having a sequence P'1 that is 3' of sequence P2 and is capable of hybridizing to primer P1. The resulting two single stranded polynucleotides (fully extended primers P1 and P2) can then be amplified by the polymerase chain reaction.

Another aspect of the present invention concerns a composition comprising a single strand of DNA comprised of a sequence T3 and a sequence T2 wherein the 3' end of T3 is contiguous with the 5' end of T2. The single strand is complexed to a blocker DNA sequence comprised of a sequence B1 complementary to T3 and a sequence S1 that is 5' of B1 and homologous to T2. The compositions can also include a primer polynucleotide having a sequence at its 3' end complexed with a sequence T1 in the single strand of DNA.

The invention further includes kits comprising in packaged combination (a) a primer polynucleotide having a sequence at its 3' end hybridizable with a first sequence T1 in a template polynucleotide, (b) a blocker polynucleotide having a sequence B1, wherein B1 is hybridizable with a sequence T3 in the template polynucleotide and wherein T3 is 3' of T1 and the 5' end of T3 is 5' of the 5' end of a sequence T2 and (c) a polynucleotide Q having sequences S1 and S2 wherein S1 is 3' of S2 and homologous to T2 in the template polynucleotide and wherein S2 is a sequence that is homologous to at least the 3' end portion of the primer.

The invention further includes kits comprising in packaged combination (a) a primer polynucleotide having a sequence at its 3' end hybridizable with a first sequence T1 in a template polynucleotide, (b) a blocker polynucleotide having a sequence B1, wherein B1 is hybridizable with a sequence T3 in the template polynucleotide wherein T3 is 3' of T1 and the 5' end of T3 is 5' of the 5' end of a sequence T2 and (c) a polynucleotide Q having sequences S1 and S2 wherein S1 is 3' of S2 and homologous to T2 in the template polynucleotide and wherein S2 is a sequence that is homologous to at least the 3' end portion of a second primer.

BRIEF DESCRIPTION OF THE DRAWINGS

FIGS. 1–7 are schematics of different embodiments in accordance with the present invention.

FIGS. 8–16 are visualizations of gels on which reaction products from the EXAMPLES were run.

DESCRIPTION OF THE SPECIFIC EMBODIMENTS

The present method allows extension of a polydeoxynucleotide primer along a single stranded (ss) template polynucleotide sequence and thereafter along another ss polynucleotide to produce a ss product polynucleotide having two or more defined sequences.

In the production of the above polynucleotide the following steps are performed: (a) a sequence B1 of a blocker polynucleotide is hybridized to a complementary sequence T3 of a template polynucleotide ("template"), wherein the 5' end of T3 is 5' of the 5' end of a sequence T2, T2 and T3 being 5' to and non-contiguous with a sequence T1, (b) the 3' end of a polynucleotide primer comprising a second defined sequence is hybridized to T1 wherein step (b) is performed prior to, after, or simultaneously with step (a), and (c) the primer is extended along the template and along at least a portion of T2, preferably along at least 8 bases of T2, more preferably up to the blocker polynucleotide and thereafter along a polynucleotide Q having sequences S1 and S2 wherein S1 is 3' of S2 and homologous with T2 to give an extended primer having a first defined nucleic acid sequence at its 3' end that is complementary to S2 and a second defined sequence that corresponds to the primer, wherein polynucleotide Q is either attached to the 5' end of (i.e., is a part of) the blocker polynucleotide or is present as a separate reagent.

One particular aspect of the invention allows for the production of a single stranded polydeoxynucleotide having a structure capable of intramolecular base-pairing, i.e., having two segments that are non-contiguous and complementary with each other, otherwise known as an inverted repeat, which can form a stem loop structure. The method has particular application in the area of single primer amplification, in which a target polynucleotide sequence in a sample is amplified when such target polynucleotide sequence has a structure capable of intramolecular base-pairing or can be converted to such a structure. The present method provides a highly convenient method for converting a polynucleotide sequence of interest to a target polynucleotide sequence having an intramolecular structure capable of base-pairing while minimizing the number of reagents and steps required.

Before proceeding further with a description of the specific embodiments of the present invention, a number of terms will be defined.

Polynucleotide analyte—a compound or composition to be measured that is a polymeric nucleotide or a portion of a polymeric nucleotide, which in the intact natural state can have about 20 to 500,000 or more nucleotides and in an isolated state can have about 30 to 50,000 or more nucleotides, usually about 100 to 20,000 nucleotides, more frequently 500 to 10,000 nucleotides. It is thus obvious that isolation of the analyte from the natural state often results in fragmentation of the polymeric nucleotide. The polynucleotide analytes include nucleic acids from any source in purified or unpurified form including DNA (dsDNA and ssDNA) and RNA, including t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like. The polynucleotide analyte can be only a minor fraction of a complex mixture such as a biological sample. The analyte can be obtained from various biological material by procedures well known in the art. Some examples of such biological material by way of illustration and not limitation are disclosed in Table A below.

TABLE A

| Microorganisms of interest include: | |
|---|---|
| Corynebacteria | |
| Corynebacterium diphtheria | |
| Pneumococci | |
| Diplococcus pneumoniae | |
| Streptococci | |
| Streptococcus pyrogenes | |
| Streptococcus salivarus | |
| Staphylococci | |
| Staphylococcus aureus | |
| Staphylococcus albus | |
| Neisseria | |
| Neisseria meningitidis | |
| Neisseria gonorrhea | |
| Enterobacteriaciae | |
| Escherichia coli | |
| Aerobacter aerogenes | The colliform |
| Klebsiella pneumoniae | bacteria |
| Salmonella typhosa | |
| Salmonella choleraesuis | The Salmonellae |
| Salmonella typhimurium | |
| Shigella dysenteria | |
| Shigella schmitzii | |
| Shigella arabinotarda | |
| | The Shigellae |
| Shigella flexneri | |
| Shigella boydii | |
| Shigella sonnei | |
| other enteric bacilli | |
| Proteus vulgaris | |
| Proteus mirabilis | Proteus species |
| Proteus morgani | |
| Pseudomonas aeruginosa | |
| Alcaligenes faecalis | |
| Vibrio cholerae | |
| Hemochilue-Bordetella group | Rhizopus ozyzae |
| Hemophilus influenza, H. ducryi | Rhizopus arrhizua Phycomycetes |
| Hemophilus hemophilus | Rhizopus nigricans |
| Hemophilus aegypticus | Sporotrichum schenkii |
| Hemophilus parainfluenza | Flonsecaea pedrosoi |
| Bordetella pertussis | Fonsecacea compact |
| Pasteurellae | Fonsecacea dermatidis |
| Pasteurella pestis | Cladosporium carrionii |
| Pasteurella tulareusis | Phialophora verrucosa |
| Brucellae | Aspergillus nidulans |
| Brucella melitensis | Madurella mycetomi |
| Brucella abortus | Madurella grisea |
| Brucella suis | Allescheria boydii |
| Aerobic Snore-forming Bacilli | Phialophora jeanselmei |
| Bacillus anthracis | Microsporum gypseum |
| Bacillus subtilis | Trichophyton mentagrophytes |
| Bacillus megaterium | Kezatincmyces ajelloi |
| Bacillus cereus | Microsporum Canis |
| Anaerobic Spore-forming Bacilli | Trichophyton rubrum |
| Clostridium botulinum | Microsporum adouini |
| Clostridium tetani | Viruses |
| Clostridium perfringens | Adenoviruses |
| Clostridium novyi | Herpes Viruses |
| Clostridium septicum | Herpes simplex |
| Clostridium histolyticum | Varicella (Chicken pox) |
| Clostridium tertium | Herpes Zoster (Shingles) |
| Clostridium bifermentans | Virus B |
| Clostridium sporogenes | Cytomegalovirus |
| Mycobacteria | Pox Viruses |
| Mycobacterium tuberculosis hominis | Variola (smallpox) |
| Mycobacterium bovis | Vaccinia |
| Mycobacterium avium | Poxvirus bovis |
| Mycobacterium leprae | Paravaccinia |
| Mycobacterium paratuberculosis | Molluscum contagiosum |
| Actinomycetes (fungus-like bacteria) | Picornaviruses |
| Actinomyces Isaeli | Poliovirus |
| Actinomyces bovis | Coxsackievirus |
| Actinomyces naeslundii | Echoviruses |
| Nocardia asteroides | Rhinoviruses |
| Nocardia brasiliensis | Myxoviruses |
| The Spirochetes | Influenza(A, B, and C) |
| Treponema pallidum Spirillum minus | Parainfluenza (1–4) |

TABLE A-continued

Microorganisms of interest include:

| | |
|---|---|
| Treponema pertenue Streptobacillus monoiliformis | Mumps Virus |
| | Newcastle Disease Virus |
| Treponema carateum | Measles Virus |
| Borrelia recurrentis | Rinderpest Virus |
| Leptospira icterohemorrhagiae | Canine Distemper Virus |
| Leptospira canicola | Respiratory Syncytial-Virus |
| Trypanasomes | Rubella Virus |
| Mycoplasmas | Arboviruses |
| Mycoplasma pneumoniae | |
| Other pathogens | Eastern Equine Eucephalitis Virus |
| Listeria monocytogenes | Western Equine Eucephalitis Virus |
| Erysipelothrix rhusicpathiae | Sindbis Virus |
| Streptobacillus moniliformis | Chikugunya Virus |
| Donvania granulomatis | Semliki Forest Virus |
| Bartonella bacilliformis | Mayora Virus |
| Rickettsia (bacteria-like parasites) | St. Louis Encephalitis Virus |
| Rickettsia prowazekii | California Encephalitis Virus |
| Rickettsia mooseri | Colorado Tick Fever Virus |
| Rickettsia rickettsii | Yellow Fever Virus |
| Rickettsia conori | Dengue Virus |
| Rickettsia australis | Reoviruses |
| Rickettsia sibiricus | Reovirus Types 1–3 |
| | Retroviruses |
| Rickettsia akari | Human Immunodeficiency Viruses |
| (HIV) | |
| Rickettsia tsutsugamushi | Human T-cell Lymphotrophic Virus I & II (HTLV) |
| Rickettsia burnetti | Hepatitis |
| Rickettsia quintana | Hepatitis A Virus |
| Chlamydia (unclassifiable parasites bacterial/viral) | Hepatitis B Virus |
| | Hepatitis nonA-nonE Virus |
| Chlamydia agents (naming uncertain) | Tumor Viruses |
| Fungi | Bauscher Leukemia Virus |
| Cryptococcus neoformans | Gross Virus |
| Blastomyces dermatidis | Maloney Leukemia Virus |
| Hisoplasma capsulatum | |
| Coccidioides immitis | Human Papilloma Virus |
| Paracoccidioides brasiliensis | |
| Candida albicans | |
| Aspergillus fumigatus | |
| Mucor corymbifer | |
| (Absidia corymbifera) | |

The polynucleotide analyte, where appropriate, may be treated to cleave the analyte to obtain a template polynucleotide that contains a target polynucleotide sequence, for example, by shearing or by treatment with a restriction endonuclease or other site specific chemical cleavage method. However, it is an advantage of the present invention that the polynucleotide analyte can be used in its isolated state without further cleavage.

For purposes of this invention, the polynucleotide analyte, or a cleaved fragment obtained from the polynucleotide analyte, is usually at least partially denatured or single stranded or treated to render it denatured or single stranded. Such treatments are well-known in the art and include, for instance, heat or alkali treatment. For example, double stranded DNA, when heated at 90°–100° C. for a period of 10–20 seconds or more, produces denatured material.

Template polynucleotide—a sequence of nucleotides, usually existing within a polynucleotide analyte, the identity of which is known to an extent sufficient to allow preparation of a polynucleotide primer, a blocker polynucleotide, and the sequence S1 in polynucleotide Q. The polynucleotide primer should be capable of hybridizing with a sequence T1 within such template polynucleotide, usually at least a 10 nucleotide segment at the 3'-end thereof and preferably at least a 15, frequently a 20 to 100 or more nucleotide segment thereof. A sequence B1 of a blocker polynucleotide should be capable of hybridizing with a sequence T3 within such template polynucleotide, usually at least a 10 nucleotide segment at the 5'-end thereof and preferably at least a 15, frequently a 20 to 100 or more nucleotide segment thereof. The template polynucleotide has three nucleotide sequences T1, T2 and T3, wherein T1 is non-contiguous and 3' of T2 and T3 and is the aforesaid portion capable of hybridizing to the polynucleotide primer. The 5' end of sequence T3 is 5' of the 5' end of sequence T2, preferably at least 10 to 15 bases, of the 5' end of sequence T2, and preferably its 3' end is contiguous with or lies within sequence T2. When the 3' end of T3 is not contiguous with or within sequence T2, it is usually less than 10 bases 5' of T2, frequently less than 5 bases 5' of T2. Sequence T2 is homologous to sequence S1 in polynucleotide Q. The target polynucleotide sequence is located between T1 and T3.

The template polynucleotide is usually a part of the polynucleotide analyte. The template polynucleotide is generally a fraction of a larger molecule but it may be substantially the entire molecule. The number of nucleotides in the template polynucleotide is determined from the sum of the nucleotides in T1, T3 and the target polynucleotide sequence. Generally, the template polynucleotide is obtained from the polynucleotide analyte by any procedure that is capable of generating smaller polynucleotides from larger polynucleotides such as, for example, digestion of the larger polynucleotide with a restriction enzyme or other site-specific chemical cleavage agent, mechanical shearing, and so forth.

The polynucleotide sequence T2 of the template polynucleotide, which is homologous with sequence S1 of the polynucleotide Q, is at least 4 nucleotides, preferably 10–30, and may be 30–100 deoxynucleotides, in length. In general T2 will be about 10 to 40 deoxynucleotides.

In a preferred embodiment at least a five base sequence within the 15 bases at the 3' end of T3 is comprised of at least 80% of G and C nucleotides.

Target polynucleotide sequence—a sequence of nucleotides to be identified, either RNA or DNA, existing within a template polynucleotide between sequences T1 and T3 of the template polynucleotide employed in the present invention. The target polynucleotide sequence is at least 20 nucleotides, usually at least 50, frequently 200–4000 nucleotides, in length. Preferably the target polynucleotide sequence is about 200 to 1200 deoxynucleotides.

The minimum number of nucleotides in the target polynucleotide sequence is selected to assure that the presence of target polynucleotide sequence in a sample is a specific indicator of the presence of polynucleotide analyte in a sample. Very roughly, the target polynucleotide sequence length is usually greater than about 1.6 log L nucleotides where L is the number of base pairs in the genome of the biologic source of the sample. The maximum number of nucleotides in the target polynucleotide sequence is normally governed by the length of the polynucleotide analyte, and its tendency to be broken by shearing, or other processes during isolation and any procedures required to prepare the sample for a ssay and the efficiency of detection and/or amplification of the sequence.

Single stranded (ss) polydeoxynucleotide sequence—a sequence of deoxynucleotides that is formed as a result of the present invention. It is normally comprised of at least two defined segments or flanking sequences that are non-contiguous with each other. The first and second defined segments or flanking sequences are at the 3'-end and 5'-end of the ss polydeoxynucleotide sequence. The first defined sequence may be complementary to the second defined sequence and/or the defined sequences may contain one or more sequences that, when bound to their complementary sequences, are specific binding sites for receptors such as repressors, restriction enzymes, and the like. The first and the second sequence each comprises at least 10, preferably at least 15, deoxynucleotides, and/or derivatives thereof.

The single stranded polydeoxynucleotide sequence usually contains from 40 to 4000 deoxynucleotides, preferably 100 to 2000 deoxynucleotides, more preferably 250 to 1250 deoxynucleotides.

Polynucleotide primer—a polynucleotide, usually a synthetic polynucleotide, which is single stranded, containing a sequence at its 3'-end that is capable of hybridizing with sequence T1, and that is preferably complementary to T1 of the template polynucleotide sequence. Although the nucleotide at the 3' end of the polynucleotide primer is usually a deoxynucleotide, the primer may comprise modified bases such as phosporothioates, methylated bases, phosphonates and the like and may also comprise ribonucleotides. The number of nucleotides in the sequence of the polynucleotide primer hybridizable with T1 should be such that stringency conditions used to hybridize the polynucleotide primer to T1 prevents excessive random non-specific hybridization. The number of nucleotides in the polynucleotide primer is at least as great as that in T1. The polynucleotide primer can contain at its 5' end nucleotides other than those in the sequence hybridizable with T1. These additional nucleotides can serve as ligands following extension and amplification of the extended primer and may, therefore, include sequences that bind to nucleic acid binding proteins, for example. They can also serve to facilitate amplification of the extended primer. For instance, they can be chosen so that the sequence is homologous to S2 and, thus, hybridizable to a polynucleotide primer that is employed in single primer amplification. The number of nucleotides other than those in the sequence hybridizable with T1 may vary widely, usually within the range of 0–2000, frequently 0–300, preferably 0–50. The primer may be labelled with a reporter molecule.

Partially Extended Primer—a sequence of deoxynucleotides normally formed as a result of the extension of the polynucleotide primer along the template polynucleotide and along at least a portion of T2, before it switches strands to extend along the polynucleotide Q. When the 3' end of T3 has a sequence in common with the 5' end of T2, the 5' end of the blocker polynucleotide sequence B1 may be displaced during extension. The partially extended primer then consists at its 3' end of bases complementary to the 3' end of T3, the 5' end of T2, and the 5' end of S1 and homologous to the 5' end of the blocker sequence B1. Whether the 5' end of the blocker is displaced by DNA polymerase depends on the temperature at which the reaction is conducted, the base content and structure of the blocker polynucleotide and also on the type of DNA polymerase employed. For example, Vent DNA polymerase, while extending the 3' end of a primer, may displace the 5' end of a specific encountered DNA polymerase at 72° C., but not at 55° C. Therefore, with this DNA polymerase at 55° C. polymerization or extension of the primer would stop at the 5' end of the blocker polynucleotide. In general, the primer extension will stop at the 5' end of the blocker more efficiently when the blocker sequence B1 is G-C rich and at lower temperatures. By controlling the temperature, the extending primer can be stopped at or near the 5' end of the blocker and then switch strands from the template to polynucleotide Q prior to further extension. Deoxynucleoside triphosphates deoxynucleosides having a 5'-triphosphate substituent. The deoxynucleosides are penrose sugar derivatives of nitrogenous bases of either purine or pyrimidine derivation, covalently bonded to the 1'-carbon of the penrose sugar. The purine bases include adenine(A), guanine(G), inosine, and derivatives and analogs thereof. The pyrimidine bases include cytosine(C), thymine (T), uracil (U), and derivatives and analogs thereof.

The derivatives and analogs include any substrate of a polydeoxynucleotide polymerase that can be incorporated into a polynucleotide through catalysis by such enzyme. The derivates and analogs are exemplified by those that are recognized and polymerized by the enzyme in a similar manner to the underivitized nucleoside triphosphates. Examples of such derivatives or analogs by way of illustration and not limitation are those that are modified with a reporter group, biotinylated, amine modified, radiolabeled, alkylated, and the like and also include phosphorothioate, phosphite, ring atom modified derivatives, unnatural bases, and the like. The reporter group can be a fluorescent group such as fluorescein, a chemiluminescent group such as luminol, a terbium chelator such as N-(hydroxyethyl) ethylenediaminetriacetic acid that is capable of detection by delayed fluorescence, and the like.

Polydeoxynucleotide polymerase—a catalyst, usually an enzyme, for forming an extension of the polynucleotide primer along a nucleic acid template that is comprised predominantly of deoxynucleotides. The polydeoxynucleotide polymerase is a template dependent polydeoxynucleotide polymerase and utilizes the deoxynucleoside triphosphates as building blocks for extending the 3' end of the polynucleotide primer to provide a sequence complementary with a single stranded polynucleotide sequence. Usually, the catalysts are enzymes, such as DNA polymerases, for example, T4 DNA polymerase, T7 DNA polymerase, Klenow fragment, reverse transcriptase, Vent DNA polymerase and Vent$_R$ (recombinant) DNA polymerase, (Vent is a trademark of New England BioLabs, Beverly, MA), Pfu DNA polymerase, and the like, derived from any source such as cells, bacteria, for example, E. coli, plants, animals, virus, thermophilic bacteria, and so forth. Where the polynucleotide Q and/or target polynucleotide sequence is RNA, reverse transcriptase is used as at least one of the polynucleotide polymerases to facilitate extension of the primer along the polynucleotide Q and/or template. of course, a polydeoxynucleotide polymerase used in the present invention for extending a primer along a single stranded template and thereafter along another single stranded polynucleotide should have little or no 5'-3' exonuclease activity so as to minimize degradation of blocker polynucleotide. The 5'-3' exonuclease activity of a polydeoxynucleotide polymerase is dependent on several factors such as pH, salt concentration, whether the template is double stranded or single stranded, and so forth, all of which are familiar to one skilled in the art. In general, the polydeoxynucleotide polymerase should not produce substantial degradation of blocker polynucleotide or primer.

Wholly or partially sequentially—when the sample and various agents utilized in the present invention are combined other than concomitantly (simultaneously), one or more may be combined with one or more of the remaining agents to form a subcombination. Each subcombination can then be subjected to one or more steps of the present method. Thus, each of the subcombinations can be incubated under conditions to achieve one or more of the desired results.

Hybridization (hybridizing) and binding—in the context of nucleotide sequences these terms are used interchangeably herein. The ability of two polynucleotide sequences to hybridize with each other is based in a large part on the degree of complementarity of the two polynucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Another factor to be considered is the nature of the nucleotide pairs that are opposite in the two strands. Some nucleotide pairs, such as G and C, have greater binding affinities for one another than do other pairs. Increased stringency is achieved by elevating the temperature, increasing the ratio of cosolvents, lowering the salt concentration, and the like.

Homologous or substantially identical—In general, two polynucleotide sequences that are identical, or at least can each hybridize to the same polynucleotide sequence, are homologous. The two sequences are homologous or substantially identical where the sequences each have at least 90%, preferably 100%, of the same or analogous base sequence where thymine (T) and uracil (U) are considered the same. Thus, the ribonucleotides A, U, C and G are taken as analogous to the deoxynucleotides dA, dT, dC, and dG, respectively. Homologous sequences can both be DNA or one can be DNA and the other RNA.

Complementary—two sequences are complementary when the sequence of one can bind to the sequence of the other in an anti-parallel sense wherein the 3' end of each sequence binds to the 5' end of the other sequence and, for example, among the natural bases each A, T(U), G, and C of one sequence is then aligned with a T(U), A, C, and G, respectively, of the other sequence.

Blocker polynucleotide—a polynucleotide, either DNA or RNA, usually a synthetic polynucleotide that is single stranded, containing a sequence B1 that is hybridizable, and preferably complementary, with sequence T3 of the template polynucleotide. The number and composition of nucleotides in the hybridizable sequence B1 of the blocker polynucleotide should be such that stringency conditions used to hybridize the blocker polynucleotide prevent excessive random non-specific hybridization. The number of nucleotides in the blocker polynucleotide is at least as great as sequence T3 of the template polynucleotide sequence. Additional nucleotides may be bound to the ends of the hybridizable sequence B1, the number being dictated primarily by considerations of cost and practicality. Thus, 0–1000 or more nucleotides may be bound to the ends, or the blocker polynucleotide could be cyclic, for example, by incorporating B1 into a plasmid or phage DNA.

As a practical matter, when the blocker polynucleotide is a synthetic oligomer, it is desirable to use a short sequence, preferably less than 100, preferably less than 50, more preferably 10–40, nucleotides. It is important that the nucleotides in the hybridizable sequence B1, particularly those at the 5' end of B1 or those that bind near the 5' end of T2, strongly bind the opposing nucleotide in sequence T3. This can be achieved in a variety of ways. Preferably, the blocker will be GC rich, particularly in the region where it binds near to the 5' end of T2. For example, it is desirable to have present at least a five base sequence within the sequence B1 that contains at least four, and preferably five, G and C nucleotides. Alternatively, the entire B1 sequence or one or more nucleotides within B1 can be ribonucleotides or may be unnatural and may include substituted nucleotides or nucleotide mimics (such as a nucleotide with an intercalation group, e.g., ethidium, attached in a manner to permit intercalation when the nucleotide is incorporated with a double stranded sequence) or a polynucleotide containing a phosphate-deleted nucleotide. The important consideration with respect to the above is that the B1 sequence binds sufficiently selectively to sequence T3 that it does not interefere with binding of the primer or chain extension of the primer along the target polynucleotide sequence or along polynucleotide Q and serves to block or impede chain extension along at least that portion of T3 that is not shared in common with T2. In one embodiment T2 is contiguous with T3.

The 3' end of the blocker polynucleotide may be the same as the 3' end of B1 or may include additional nucleotides or substituents, for example, to prevent chain extension catalyzed by the polydeoxynucleotide polymerase.

Polynucleotide Q—a single stranded polynucleotide, usually a synthetic oligonucleotide, either attached to the 5' end of a blocker polynucleotide or present as a separate reagent. Polynucleotide Q may be DNA or RNA, preferably DNA, and is comprised of two sequences of nucleotides. One of such sequences (S1) is 3' of the other of such sequences (S2) and is homologous with sequence T2. The 5' end of S1 is complementary to the 5' end of sequence B1 when the 5' end of T2 overlaps the 3' end of T3. The major criteria for choosing S1 is that the sequence should be reliable, that is, it should be sufficiently homologous to T2 that it will bind specifically to the 3' end of a DNA sequence composed of a sequence complementary to T2 to an extent at least sufficient to permit polynucleotide polymerase catalyzed extension of the DNA sequence along polynucleotide Q. The number of nucleotides in sequence S1 is equal to the number of nucleotides in the T2 sequence of the template polynucleotide sequence. When the T2 sequence is selected, for example 4–12 nucleotides, it is sometimes desirable to include multiple copies of S1 arranged in tandem in polynucleotide Q, usually 2–6 copies. The presence of multiple copies of S1 is not essential but can in some instances increase the yield of single stranded polydeoxynucleotide with two defined sequences. Preferably, S1 is from 5–50 nucleotides in length. In one embodiment a sequence comprising the 5' end of S1 is complementary to a sequence comprising the 5' end of B1. In an alternative embodiment these sequences are not complementary.

The second polynucleotide sequence of polynucleotide Q, designated S2, is a sequence of nucleotides that is 5' of S1 and may or may not be contiguous with S1. S2 is complementary to and thereby defines the first defined sequence that is to be introduced at the 3' end of the extended primer. S2 may contain a sequence that is substantially identical or homologous to at least the 3' end of the polynucleotide primer and/or contain one or more sequences which, when bound to their complementary sequences, are specific binding sites for receptors such as repressors, restriction enzymes, and the like. S2 is at least 10 nucleotides, usually at least 15, preferably 20–50 deoxynucleotides, in length. In general, S2 will be about 10 to 2000 or more deoxynucleotides depending on the first defined sequence that is desired.

In the situation where polynucleotide Q is present as a separate reagent, it is sometimes desirable to prevent extension of the 3' end of polynucleotide Q along the extended polynucleotide primer. This may be avoided by appending to the 3' end of S1 one or more nucleotides that are not complementary to the nucleotides in the target polynucleotide sequence contiguous with the 3' end of T2. Additionally or alternatively, the 3' end can be modified by phosphylation, introduction of a dideoxynucleotide or a basic ribophosphate, attachment to a polymer or surface, or other means for inhibiting chain extension. All of the above procedures for such modification are well known in the art. Furthermore, other procedures for such modifications will be suggested to those skilled in the art.

In the situation where polynucleotide Q is attached to the 5' end of the blocker polynucleotide, the sequence S1 may be contiguous to sequence B1 or be separated by any convenient number of nucleotides, usually 0–100, preferably 0–40, more preferably 0–20.

Polynucleotide Q may contain additional spacer sequences or other sequences located between S1 and S2 or at the end of S2.

Non-contiguous—sequences are non-contiguous, there being at least one, usually at least 10, nucleotides between the two sequences.

Contiguous—sequences are considered to be contiguous when there are no nucleotides between the two sequences.

Copy—a sequence that is identical to or homologous with a single stranded polynucleotide sequence as differentiated from a sequence that is complementary to or hybridizable with the sequence of such single stranded polynucleotide. In single primer amplification described above in the background section, a complementary sequence of a single stranded polydeoxynucleotide sequence is produced initially as the result of the extension of a polynucleotide primer, and a sequence that is identical to or homologous with the single stranded polydeoxynucleotide sequence is subsequently obtained from further extension of the polynucleotide primer along the aforementioned complementary sequence.

Means for extending a primer—a polynucleotide polymerase or a single stranded template polynucleotide having a sequence other than at its 3' end that can hybridize to at least the 3' end of the primer or both. Means for extending a primer also includes nucleoside triphosphates or analogs thereof capable of acting as substrates for the enzyme and other materials and conditions required for enzyme activity such as a divalent metal ion (usually magnesium), pH, ionic strength, organic solvent (such as formamide), and the like.

Member of a specific binding pair ("Sbp member")—one of two different molecules, having an area on the surface or in a cavity that specifically binds to and is thereby defined as complementary with a particular spatial and polar organization of the other molecule. The members of the specific binding pair are referred to as ligand and receptor (antiligand). These may be members of an immunological pair such as antigen-antibody, or may be operator-repressor, nuclease-nucleotide, biotin-avidin, hormones-hormone receptors, nucleic acid duplexes, IgG-protein A, DNA-DNA, DNA-RNA, and the like.

Ligand—any compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, repressors, protection enzymes, protein A, complement component C1q, DNA binding proteins or ligands and the like.

Small organic molecule—a compound of molecular weight less than 1500, preferably 100 to 1000, more preferably 300 to 600 such as biotin, fluorescein, rhodamine and other dyes, tetracycline and other protein binding molecules, and haptens, etc. The small organic molecule can provide a means for attachment of a nucleotide sequence to a label or to a support.

Support or surface—a porous or non-porous water insoluble material. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials; gla ss available as Biogla ss, ceramics, metals, and the like. Natural or synthetic a ssemblies such as liposomes, phospholipid vesicles, and cells can also be employed.

Binding of sbp members to the support or surface may be accomplished by well-known techniques, commonly available in the literature. See, for example, "Immobilized Enzymes," Ichiro chibata, Halsted Press, New York (1978) and Cuatrecasas, *J. Biol, Chem.*, 245:3059 (1970). The surface can have any one of a number of shapes, such as strip, rod, particle, including bead, and the like.

Label or reporter group or reporter molecule—a member of the signal producing system. Usually the label or reporter group or molecule is conjugated to or becomes bound to a polynucleotide probe or a polynucleotide primer and is capable of being detected directly, or indirecting by being bound through a specific binding reaction, to a detectable substance. Labels able to be detected indirectly include polynucleotides such as a polynucleotide primer or a specific polynucleotide sequence that can act as a ligand for a complementary polynucleotide or provide a template for amplification or ligation or act as a ligand such as for a repressor protein; haptens; antibodies; receptors such as avidin; ligands such as biotin and the like. Labels able to be detected directly may be isotopic or nonisotopic, usually non-isotopic, and can be a catalyst, such as an enzyme, ribozyme, a substrate for a replicase such as QB replicase, promoter, dye, fluorescent molecule, chemiluminescer, coenzyme, enzyme substrate, radioactive group, a particle such as latex or carbon particle, metal sol, crystallite, liposome, cell, etc., which may or may not be further labeled with a dye, catalyst or other detectible group, and the like. The label is a member of a signal producing system and can generate a detectable signal either alone or together with other members of the signal producing system. The label can be bound directly to a nucleotide sequence or can become bound thereto by being bound to an sbp member complementary to an sbp member that is bound to a nucleotide sequence.

Signal Producing System—The signal producing system may have one or more components, at least one component being the label or reporter group. The signal producing system generates a signal that relates to the presence or amount of target polynucleotide sequence or a polynucleotide analyte in a sample. The signal producing system includes all of the reagents required to produce a measurable signal. When the label is not conjugated to a nucleotide sequence, the label is normally bound to an sbp member complementary to an sbp member that is bound to or part of a nucleotide sequence. Other components of the signal producing system may be included in a developer solution and can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, such as detection of electromagnetic radiation, desirably by visual examination. The signal-producing system is described more fully in U.S. patent application Ser. No. 07/555,323, filed Jul. 19, 1990, the relevant disclosure of which is incorporated herein by reference.

Ancillary Materials—Various ancillary materials will frequently be employed in the method in accordance with the present invention. For example, buffers will normally be present in the medium, as well as stabilizers for the medium and the reaction components. Frequently, in addition to these additives, proteins may be included, such as albumins, organic solvents such as formamide, quaternary ammonium salts, polycations such as dextran sulfate, surfactants, particularly non-ionic surfactants, binding enhancers, e.g., polyalkylene glycols, or the like.

One embodiment of the method is depicted schematically in FIG. 1. The 3' end of polynucleotide primer P comprising sequence S3 hybridizes with T1 of template polynucleotide A. A sequence B1 located at the 5' end of a blocker polynucleotide B hybridizes with T3 of template polynucleotide A having sequences T1, T2 and T3. The 3' end of T3 lies within T2. T2 is homologous with sequence S1 of polynucleotide Q. Polynucleotide Q is attached to, i.e., is a continuing sequence of nucleotides in, the 5' end of the blocker polynucleotide and contains sequences S1 and S2. The 5' end of S1 is complementary to the 5' end of B1. S2 in this example is homologous to S3. In the presence of deoxynucleoside triphosphates and DNA polymerase and under appropriate reaction conditions, the primer is extended along the template and along a portion of T2. Under the reaction conditions at least the 3' end of the extended primer dissociates from the template at T2, hybridizes to S1 and extends along the polynucleotide Q to produce an extended primer D. The extended primer contains sequence S'2, which is complementary to S2 and, in this example, to S3. After dissociation from its duplex the product, ss polydeoxynucleotide D, is obtained, which product contains a first defined sequence S'2 and a second defined sequence S3 that are hybridizable with each other.

A variation in the above embodiment is depicted in FIG. 2. In this case in the presence of deoxynucleoside triphosphates and DNA polymerase and under appropriate reaction conditions, the primer is extended along the template and along T2. Under the reaction conditions the polymerase partially displaces the 5' end of the blocker and the primer extends along the full length of T2. The 5' end of S1 is complementary to the 5' end of B1. The partially extended primer then switches strands, hybridizes to S1 and extends along the polynucleotide Q to produce an extended primer E containing sequence S'2, which is complementary to S2 and, in this example, to S3. E now contains S3 and S'2, which are hybridizable with each other.

Another variation in the above embodiment is depicted schematically in FIG. 3. In this case the polynucleotide Q is present as a separate reagent. The sequence B1 in the blocker and S1 in polynucleotide Q do not have complementary 5' ends. The sequence B1 in the blocker is complementary to T3 of template polynucleotide A, which has sequences T1, T2 and T3. The 3' end of T3 is contiguous with T2, both of which are 5' of and not contiguous with T1. In the presence of deoxynucleoside triphosphates and DNA polymerase and under appropriate reaction conditions, the primer hybridizes with T1 and is extended along the template and along at least a portion of T2. Under the reaction conditions the partially extended primer switches strands, hybridizes to S1 and extends along polynucleotide Q to produce an extended primer F containing sequence S'2, which is complementary to S2. When S2 is designed to be homologous with S3, S'2 is also complementary to S3. F now contains the defined sequences S3 and S'2, which are hybridizable with each other. In a variation of the above method the polynucleotide Q is the 5' portion of a larger polynucleotide comprising the blocker polynucleotide B. The extending primer extends along at least a portion of T2 prior to switching strands as shown in FIG. 1.

Another embodiment of the invention is depicted in FIG. 4. In this embodiment the sequence T2 in the template polynucleotide A is not contiguous with sequence T3. Also, the 5' ends of sequences S1 and B1 in polynucleotide Q are not complementary. Under suitable reaction conditions the primer is extended along the template and along at least a portion of T2 before it switches strands, hybridizes to S1 and extends along polynucleotide Q to produce the extended primer G. In a variation of the above approach, polynucleotide Q may be present as a separate reagent not attached to the blocker polynucleotide.

Another embodiment of the present invention is depicted in FIG. 5. In this embodiment T2 is homologous with S1 of the polynucleotide Q and the 5' end of T3 is 5' of the 5' end of T2 and the 3' end of T3 lies within T2. In this embodiment the entire S1 sequence is complementary to the 5' end of B1. The primer is extended along the template and along at least a portion of T2, which comprises the 3' end of T3. Under appropriate reaction conditions the extending primer switches strands, hybridizes to S1 and extends along polynucleotide Q to produce extended primer H. Polynucleotide Q can be present as a reagent separate from the blocker polynucleotide in an alternative embodiment of the invention.

Another embodiment of the invention is shown in FIG. 6. Polynucleotide Q is present as a separate reagent from the blocker polynucleotide B. The 5' end of sequence T3 is 5' of the 5' end of sequence T2. Sequence S1 is homologous to T2 and B1 is complementary to T3. Under appropriate reaction conditions the primer binds to T1 and is extended along at least a portion of T2. The extended primer then switches strands and hybridizes with S1 and extends along polynucleotide Q to produce extended primer J.

The methods of the invention have application in any situation where a single stranded polynucleotide containing defined sequences is desired. Such a situation may be, for example, where it is desired to append flanking sequences to a polynucleotide to a ssist in insertion into a cloning vector, particularly where long strands are employed making it difficult to find suitable restriction enzymes. Introduction of defined sequences is also useful for mutagenesis studies, and for polymerase dependent amplifications methods such as PCR and single primer amplification.

The methods find particular use in single primer amplification, described above, wherein one or more copies of a target polynucleotide sequence, located between sequences T1 and T2 of a template polynucleotide, are formed. The use of the present method in single primer amplification is depicted in FIG. 7. Polydeoxynucleotide primer P has a sequence at its 3'-end (S3) that hybridizes with S'2 of extended primer produced as described above in FIGS. 1–6. S'2 is complementary to S2 of the polynucleotide Q. Preferably, S3 is a sequence identical to S2. P can also comprise a label or reporter molecule W. P is hybridized with and extended along extended primer D (FIG. 1), E (FIG. 2), F (FIG. 3), G (FIG. 4), H (FIG. 5) or J (FIG. 6), and is then dissociated from its duplex, to form extended primer K comprising sequences S3 and S'2, wherein S3 is complementary to S'2. Extended primer K is dissociated from its duplex and P hybridizes with S'2 and extends along the extended primer and D, E, F, G, H or J to yield $K^1$ and K, respectively. $K^1$ is complementary to K. The duplexes are dissociated and P is hybridized with and extended along $K^1$ and K to yield $K^1$ and $K^2$. Further repetition results in multiple copies of $K^1$ and $K^2$, which can be detected because of the presence of label W.

When the present method is applied to replicating a target polynucleotide sequence, one of the above described embodiments is utilized and the following steps are repeated at least once: (a) the polynucleotide primer is caused to hybridize with and extend along the extended primer to form a second duplex comprising extended primer and (b) the extended primer is dissociated from the second duplex. Normally, this process will be repeated at least three times. Preferably, the polynucleotide primer contains at least a fifteen deoxynucleotide sequence S3 capable of hybridizing with a sequence complementary to S2. Preferably, T1 and S2 each respectively contain from 10 to 100 nucleotides.

The method has application where the target polynucleotide sequence is DNA or RNA. In one aspect the polynucleotide primer is labeled with a reporter molecule. The reporter molecule can be, for example, a detectable group or a binder such as biotin or a nucleotide sequence other than the sequence that hybridizes with the sequence complementary to S2. The extended primer can be detected by means of a reporter molecule covalently bonded to a probe. The probe will usually have a nucleotide sequence that is homologous or complementary to a portion of the target nucleotide sequence between T1 and T2.

Another embodiment of the invention concerns a method for detecting the presence of a polynucleotide analyte, comprising a template sequence, in a medium suspected of containing the polynucleotide analyte. The template sequence has three sequences T1, T2 and T3 wherein T1 is non-contiguous with and 3' of T2 and T3 and wherein the 5' end of T3 is 5' of the 5' end of T2. The medium is combined with a polynucleotide primer whose 3' end is hybridizable with T1. A blocker polynucleotide with sequence B1, wherein B1 is hybridizable with T3 is also included. A polynucleotide Q having sequences S1 and S2 is attached to the 5' end of the blocker polynucleotide or is present as a separate reagent. S1 is 3' of S2 and is homologous to T2. S2 is homologous to at least the 3' end of the primer polynucleotide. Deoxynucleoside triphosphates and one or more polydeoxynucleotide polymerases are employed. Conditions are chosen such that (A) the blocker becomes hybridized to the template sequence, (B) the primer becomes hybridized with and is extended along the template sequence and along at least a portion of T2 and thereafter along the polynucleotide Q to form a duplex, (C) the extended primer is dissociated from the duplex, and (D) the primer hybridizes with and is extended along the extended primer to form a duplex comprising extended primer and steps (C) and (D) are repeated. Then, an examination is conducted for the presence of the extended primer, the presence thereof indicating the presence of the polynucleotide analyte. Steps (C) and (D) are repeated a least 1 time, preferably, at least 10 times; usually it is preferable that the number of repetitions be less than 60. Generally, steps (C) and (D) are repeated a number of times sufficient to provide an accurate detection of the polynucleotide analyte. Where the polynucleotide analyte is RNA, it can first be converted to DNA by means of a primer and reverse transcriptase, or the polydeoxynucleotide polymerase used in at least step B can be reverse transcriptase.

Appropriate reaction conditions are chosen for carrying out the method of forming the single stranded polydeoxynucleotide using a primer, and amplification if desired. The following description sets forth such appropriate conditions, which are subject to modification by those skilled in the art depending on the specific reagents and other molecules chosen for any particular application.

Generally, an aqueous medium is employed. Other polar cosolvents may also be employed in the medium, usually oxygenated organic solvents of from 1–6, more usually from 1–4, carbon atoms, including alcohols, ethers and the like. Usually, these cosolvents are present in less than about 70 weight percent, more usually, in less than about 30 weight percent.

The pH for the medium is usually in the range of about 5.5 to 10, more usually, in the range of about 6.5–9.5, and, preferably, in the range of about 7–9. The pH and temperature are chosen and varied, as the case may be, so as to cause, either simultaneously or wholly or partially sequentially, dissociation of any internally hybridized sequences, hybridization of the primer with the template polynucleotide and extended primer once the primer has been extended, extension of the primer along the template including some or all of sequence T2 but not past T2, dissociation of the partially extended primer from the template polynucleotide and hybridization of the partially extended primer to polynucleotide Q, and dissociation of the extended primer from its duplex. In some instances, a compromise will be made in optimizing the speed, efficiency, and specificity of these steps depending on whether it is desired to perform the above steps wholly or partially sequentially or simultaneously. Various buffers may be used to achieve the desired pH and maintain the pH during the determination. Illustrative buffers include borate, phosphate, carbonate, Tris, barbital and the like. The particular buffer employed is not critical to this invention but in individual methods one buffer may be preferred over another.

Moderate temperatures are normally employed for carrying out the method. As mentioned above, appropriate reaction conditions are chosen in order to achieve extension of the primer along the template onto sequence T2 while minimizing the extension of the extending primer into the region of the template 5' of T2 followed by strand switching of the extending primer from the template to polynucleotide Q. These reaction conditions are dependent on a number of considerations such as, for example, the salt concentration and the pH of the medium, the solvent composition of the medium used, the length of the target polynucleotide sequence and the length and nucleotide composition of sequences S1 and B1 and of the primer. The temperature for extension of the primer depends on the activity of the polymerase and can range from 5° to 90°, usually 25° to 80°, frequently 40° to 70° C. Strand switching may comprise a melting step where the extended primer is dissociated from the template polynucleotide and a hybridization step when it hybridizes to S1. The melting step temperature uaually is 45° to 100°, more usually 70° to 98° C. The hybridization step temperature is usually 25° to 80° C., more usually 35° to 70° C. Strand switching can also occur without the melting step whereupon the temperature for strand switching is usually 35° to 90° C., preferably 45° to 80° C., frequently 50° to 75° C.

Normally, in conducting the method of the invention in conjunction with amplification, the medium is cycled between two or three temperatures. The temperatures for the present method in conjunction with amplification generally range from about 10° to 105° C., more usually from about 40° to 99° C., preferably 50° to 98° C. As with the method of the invention itself, the temperatures utilized can be varied depending on the salt concentration, pH, solvents used, length of the target polynucleotide sequence and of sequences S1 and S2 and nucleotide composition of the target and/or template polynucleotide sequence and the primer. Relatively low temperatures of from about 30° to 65° C. can be employed for the extension steps, while denaturation and hybridization can be carried out at a temperature of from about 50° to 105° C.

In some situations it is desirable to cause hybridization and extension to occur only after denaturation of the template polynucleotide is complete. This has the advantage of increasing the fidelity of replication and can be achieved by preheating the template to at least 80° C., preferably 90°–100° C., prior to combining it with the polymerase and/or nucleoside triphosphates that will usually also be preheated.

Where the present method is utilized in amplification of a polynucleotide sequence using one or more primers, the method is conducted for a time sufficient to achieve a desired number of copies of the extended primer or a sequence complementary thereto. This, in turn, depends on the purpose for which the amplification is conducted, such as, for example, an assay for a polynucleotide analyte. Generally, the time period for conducting the method is from about 20 seconds to 10 minutes per cycle and any number of cycles can be used from 1 to as high as 200 or more, usually 5 to 80, frequently 10–60. As a matter of convenience it is usually desirable to minimize the time period and the number of cycles. In general, the time period for a given degree of amplification can be shortened, for example, by selecting concentrations of nucleoside triphosphates sufficient to saturate the polynucleotide polymerase and by increasing the concentrations of polynucleotide polymerase and polynucleotide primer. Generally, the time period for conducting the method is from about 5 to 200 minutes. As a matter of convenience, it will usually be desirable to minimize the time period. The above conditions may also be chosen for forming a template polynucleotide sequence from a polynucleotide analyte as mentioned above.

The amount of the template polynucleotide can be as low as one or two molecules in a sample but generally varies from about $10^2$ to $10^{14}$, more usually from about $10^3$ to $10^8$ molecules in sample volumes that may be less than a microliter but will usually be 1–1000 μL, more usually 5–250 μL. The amount of the polynucleotide primer should be at least as great as the number of copies desired and is usually present in at least $10^{-9}$M, preferably $10^{-7}$M, and more preferably at least about $10^{-6}$M. Preferably, the concentration of the polynucleotide primer is substantially in excess over, preferably at least 100 times greater than, the concentration of the single stranded polynucleotide.

The concentration of the deoxynucleoside triphosphates in the medium can vary widely; preferably, these reagents are present in an excess amount. The deoxynucleoside triphosphates are usually present in $10^{-6}$ to $10^{-2}$M, preferably $10^{-5}$ to $10^{-1}$.

The concentration of the blocker polynucleotide is usually at least as high as the template polynucleotide but preferably is at least $10^{-9}$M, normally $10^{-7}$ to $10^{-8}$M. The polynucleotide Q, when not attached to the blocker, is preferably at least $10^{-9}$M, normally at least $10^{-3}$M, most preferably at least $10^{-6}$M.

The concentration of the template-dependent polynucleotide polymerase is usually determined empirically. Preferably, a concentration is used that is sufficient such that further increase in the concentration does not decrease the time for the amplification by over 5-fold, preferably 2-fold. The primary limiting factor generally is the cost of the reagent.

The order of combining of the various reagents to form the combination may vary. Generally, the template polynucleotide is obtained from genetic material, DNA or RNA, from an organism or cell or from artificial constructs produced by molecular biological techniques. Generally, the template polynucleotide, the primer, the polynucleotide Q and the blocker polynucleotide are combined with a pre-prepared combination of deoxynucleoside triphosphates, and template-dependent polydeoxynucleotide polymerase. However, simultaneous addition of all of the above, as well as other step-wise or sequential orders of addition, may be employed.

The concentration and order of addition of reagents and conditions for the method are governed generally by the desire to create a single stranded polydeoxynucleotide, having defined sequences, from a polynucleotide primer and a template polynucleotide. When the present method is used in conjunction with amplification of a polynucleotide sequence using one or more primers, one consideration is to maximize the number of copies of the extended primer and the rate at which such copies are formed and the fidelity of replication. Generally, it is desirable to increase the number of copies of the extended primer by at least a factor of $10^2$, preferably a factor of $10^4$, more preferably $10^6$ or more.

In carrying out the method of the invention as applied to the detection of a polynucleotide analyte, the considerations as to media, pH, temperature, and times are as described above. While the concentrations of the various reagents will generally be determined by the concentration range of interest of the polynucleotide analyte, the final concentration of each of the reagents will normally be determined empirically to optimize the sensitivity of the assay over the range of interest. The concentration of the other reagents in an assay generally will be determined following the same principles as set forth above for the amplification method. The primary consideration is that a sufficient number of copies of extended primer be produced in relation to the polynucleotide analyte so that such copies can be readily detected and provide an accurate determination of the polynucleotide analyte if present.

The copies of extended primer can be detected in numerous ways. For example, in the present method, molecules of the polynucleotide primer can be labeled with a reporter molecule such as a ligand, a small organic molecule, a polynucleotide sequence, a polypeptide, a support, an operator or the like. Examples of particular labels or reporter molecules and their detection can be found in U.S. patent application Ser. No. 07/555,323 filed Jul. 19, 1990, the relevant disclosure of which is incorporated herein by reference. Other assay formats and detection formats are disclosed in U.S. patent applications Ser. Nos. 07/299,282 and 07/399,795 filed Jan. 19, 1989, and Aug. 29, 1989, respectively, which have been incorporated herein by reference. Any standard method for specifically detecting nucleic acid sequences can be used.

One method for detecting nucleic acids is to employ nucleic acid probes. One method utilizing such probes is described in U.S. Pat. No. 4,868,104, the disclosure of which is incorporated herein by reference.

Detection of the signal depends upon the nature of the signal producing system utilized. If the label or reporter group is an enzyme, additional members of the signal producing system would include enzyme substrates and so forth. The product of the enzyme reaction is preferably a luminescent product, or a fluorescent or non-fluorescent dye, any of which can be detected spectrophotometrically, or a product that can be detected by other spectrometric or electrometric means. If the label is a fluorescent molecule the medium can be irradiated and the fluorescence determined. Where the label is a radioactive group, the medium can be counted to determine the radioactive count.

Various techniques can be employed for preparing the polynucleotide primer, blocker polynucleotide, the polynucleotide Q or other polynucleotide sequences utilized in the present invention. Such sequences can be obtained by biological synthesis or by chemical synthesis. For short sequences (up to about 100 nucleotides) chemical synthesis is frequently more economical as compared to biological synthesis. In addition to economy, chemical synthesis provides a convenient way of incorporating low molecular weight compounds and/or modified nucleotides or bases during the synthesis step. Furthermore, chemical synthesis is very flexible in the choice of length and region of the target polynucleotide binding sequence. The polynucleotide primer, the blocker polynucleotide the polynucleotide Q and other polynucleotides can be synthesized by standard methods such as those used in commercial automated nucleic acid synthesizers. chemical synthesis of DNA or RNA on a suitably modified gla ss or resin can result in DNA or RNA covalently attached to the surface. This offers advantages in washing and sample handling. For longer sequences standard replication methods employed in molecular biology can be used such as the use of M13 for single stranded DNA as described by J. Messing, *Methods Enzymol* (1983) 101:20-78.

In addition to standard cloning techniques, in vitro enzymatic methods may be used such as polymerase catalyzed reactions. For preparation of RNA, T7 RNA polymerase and a suitable DNA template can be used. For DNA, polymerase chain reaction (PCR) and single primer amplification are convenient.

Other chemical methods of polynucleotide or oligonucleotide synthesis include phosphotriester and phosphodiester methods (Narang, et al., *Meth. Enzymol* (1979) 68:90) and synthesis on a support (Beaucage, et al., *Tetrahedron* (1981) *Letters* 22:1859-1862) as well as phosphoramidate technique, Caruthers, M. H., et al., "Methods in Enzymology," Vol. 154, pp. 287-314 (1988), and others described in "Synthesis and Applications of DNA and RNA," S. A. Narang, editor, Academic Press, New York, 1987, and the references contained therein.

The design and preparation of the blocker polynucleotide is important in performing the methods of this invention. It is preferable that the B1 sequence be rich in guanine (G) and cytidine (C). Series of G's and C's relatively uninterrupted by A's and T's are particularly useful because their tight binding inhibits dissociation during primer extension and strand switching. Accordingly, the blocker polynucleotide should preferably contain at least 50% GC composition, preferably at least 60% GC composition. Other techniques to inhibit dissociation can be used such as providing the polynucleotide blocker with one or more covalently attached small molecules that can intercalate into or otherwise bind the double strand comprising B1 hybridized to T3. A large variety of small molecule binders are available such as ethidium, acridinium, and phenazinium ions, psoralin, daunomycin, mitomycin and the like. In the situation where a photoactive small molecule is used such as psoralin, additional enhancement of binding can be achieved by irradiation of the medium with light that is absorbed by the small molecule when the irradiation is carried out following hybridization of the blocker with the template. In each of these preparations the small molecule may be attached to any convenient atom of a base, e.g., the 8 position of G or A or the 4-amino group of C or the 5-methyl group of T, or the group may be attached to a ribose carbon or to a phosphate, for example, by alkylation of a phosphorothioate. Alternatively, the blocker may be synthesized with alternative atoms in place of the phosphate linkages. In particular, uncharged linkers can provide tighter binding to a complementary strand. Uncharged linkers that can be used are phosphonates, phosphites, amides, methylene dioxy groups and the like. The synthesis of these types of oligonucleotide analogs are known in the art.

A blocker polynucleotide containing at least one phosphorothioate diester can be prepared according to known techniques. Oligonucleotide synthesis can be carried out as described above up to the point where introduction of the phosphorothioate diester is desired. The phosphorothioate diester can be introduced in a number of ways such as, for example, oxidations utilizing a thiolating reagent such as a diacyldisulfide or tetraethyl thiuram disulfide, which are commercially available. The remaining nucleotides are then introduced. Other methods of preparing phosphorothioate containing polynucleotides are described in WO9008838, WO8911486, U.S. Pat. No. 4,910,300, EP318245, the relevant disclosures of which are incorporated herein by reference. Other methods of preparing a phosphorothioate containing polynucleotide are described by (a) Yau, et al., *Tetrahedron Lett.* (1990)31(14): 1953-1956; (b) Brill, et al., ibid. (1989) 30(48):6621-6624; (c) Caruthers, et al., *Nucleic Acids Symp. Ser.* (1989)21:119-120; (d) Caruthers, et al., *Nuclgosides Nucleotides* (1988)8(5-6): 1011-1014; (e) Brill, et al., *J. Am, Chem. Soc.* (1989)111(6): 2321-2322.

As mentioned above, in some instances the 3'-end of a polynucleotide is modified to prevent reaction with template dependent DNA polymerase or to append a binding sequence. Usually, a DNA tail on the 3' end is all that is necessary. However, the 3'-end can be modified, for example, by introducing an abasic ribophosphate or other unnatural group at the 3' end during solid phase synthesis or introduction of a dideoxynucleotide or a ribonucleotide followed by oxidation of the ribose with periodate followed by reductive amination of the resulting dialdehyde with borohydride and a bulky amine such as aminodextran. The details for carrying out the above modifications are well-known in the art and will not be repeated here.

Another embodiment of the present invention concerns a method for producing from a polynucleotide primer a single stranded polydeoxynucleotide that has two different defined sequences, for example, P1 and P'2. A template polynucleotide (template) is employed having three sequences T1, T2 and T3. T1 is non-contiguous with and 3' of T2 and T3. The 3' end of T3 is contiguous with or lies without T2. The method utilizes a polynucleotide primer P1 whose 3' end is hybridizable with T1. A blocker polynucleotide is also employed and has sequence B1, wherein B1 is hybridizable with T3. Polynucleotide Q has sequences S1 and S2 and is either attached to the 5' end of the blocker polynucleotide or present as a separate reagent. S1 is 3' of S2 and homologous to T2. S2 is a sequence complementary to a sequence different from P1, such as a sequence P'2 that is complementary to a second polydeoxynucleotide primer P2. The combination is subjected to conditions for extending the primer P1 along the template and along at least a portion of T2 and thereafter along polynucleotide Q, dissociating partially extended primer P1 from its respective duplex, hybridizing partially extended primer P1 to polynucleotide Q. The extended primer M is dissociated from its duplex. A second single stranded polydeoxynucleotide N is formed by hybridizing a polydeoxynucleotide primer P2 to sequence P2 of the extended primer M and extending P2 along M and dissociating the second extended primer N from its duplex. The second extended primer N is characterized by having a sequence P'1 that is 3' of sequence P2 and is capable of hybridizing to primer P1. The resulting two single stranded polynucleotides M and N (fully extended primers P1 and P2) can then be amplified by the polymerase chain reaction, which is described in, for example, U.S. Pat. Nos. 5,008,182, 4,965,188, 4,800,159, 4,683,195 and 4,683,202, the relevant disclosures of which are incorporated hereing by reference. The conditions and reagents for accomplishing this aspect of the invention, including PCR amplification, are similar to those described above for the extension of primers in accordance with the present invention. Primer P2 hybridizes to P'2 of M and is extended along M and primer P1 hybridizes to P'1 of N and is extended along N. The extended primers are dissociated from their respective duplexes and are characterized in that each serves as a template for the other primer in a PCR amplification.

As a matter of convenience, predetermined amounts of reagents employed in the present invention can be provided in a kit in packaged combination. For use in accordance with the method of the present invention for forming a single stranded polynucleotide having defined sequences, the kit can comprise a polynucleotide primer, a blocker polynucleotide and a polynucleotide Q, which can be attached to the blocker polynucleotide or be unattached. These components can be provided as separate reagents or combined, preferably combined. In assaying for a polynucleotide analyte in a sample, a kit useful in the present method can comprise, in packaged combination with other reagents, (a) reagents for obtaining, from the polynucleotide analyte, a template polynucleotide sequence having sequences T1, T2 and T3 wherein T1 is 3' of T2 and T3 and T3 comprises of at a portion of T2, wherein such reagent may be, for example, a restriction enzyme, (b) at least one labeled or unlabeled primer having at its 3' end a sequence hybridizable with a first sequence T1 in a template polynucleotide sequence, (c) a blocker polynucleotide having sequence B1 hybridizable with sequence T3 in the template polynucleotide, and (d) a polynucleotide Q having sequences S1 and S2 wherein S1 is 3' of S2 and homologous to T2 in the template polynucleotide and wherein S2 is homologous to at least the 3' end portion of the primer, wherein polynucleotide Q is either attached to the 5' end of the blocker polynucleotide or present as a separate reagent.

The kit can further include a labeled or unlabeled polynucleotide probe capable of binding to the template polynucleotide sequence or to extended primer produced in the method of the invention. The kits above can further include in the packaged combination deoxynucleoside triphosphates (dNTPs) such as, e.g., deoxyadenosine triphosphate (dATP), deoxyguanosine triphosphate (dGTP), deoxycytidine triphosphate (dCTP) and deoxythymidine triphosphate (dTTP) or derivatives or analogs of the above. The kit can further include a polydeoxynucleotide polymerase and members of a signal producing system and also various buffered media, some of which may contain one or more of the above reagents.

In another embodiment of the invention the polynucleotide Q can have sequences S1 and S2 wherein S1 is 3' of S2 and homologous to T2 in the template polynucleotide and wherein S2 is homologous to at least the 3' end portion of a second primer. This latter kit finds use in, for example, PCR amplification.

The relative amounts of the various reagents in the kits can be varied widely to provide for concentrations of the reagents that substantially optimize the reactions that need to occur during the present method and to further substantially optimize the sensitivity of any assay, in which the present method is employed. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. Each reagent can be packaged in separate containers or some reagents can be combined in one container where cross-reactivity and shelf life permit.

EXAMPLES

The invention is demonstrated further by the following illustrative examples. Temperatures are in degrees centigrade (°C.) and parts and percentages are by weight unless otherwise indicated.

Example 1

Synthesis of Single Stranded Polynucleotide Having a Stem Loop Structure

Part A

Materials

Polynucleotide extender primer with and without 5'$^{32}$P label (Ext. Primer and 32P Ext. Primer, respectively):
Oligomer 1 (50-mer)

5'-AGC-CAT-GTT-TCG-GAA-CAC-CTA-TGC-TCG-CTT-CTG-GTG-CCG-GAA-ACC-AGG-CA- 3' (SEQ ID NO:1)

GC Blocker with and without 5'$^{32}$P label (GC Blocker and 32P-GC Blocker, respectively);
Oligomer 2 (40-mer)

5'-GCG-GGC-CTC-TTC-GCT-ATT-ACG-CCA-GCT-GGC-GAA-AGG-GGG-A-3' (SEQ ID NO:2)

AB Blocker with and without 5'$^{32}$P label (AB Blocker and 32P-AB Blocker, respectively):
Oligomer 3 (80-mer)

5'-AGC-CAT-GTT-TCG-GAA-CAC-CTA-TGC-TCC-CGC-ACC-GAT-CGC-CGC-GGG-CCT-CTT-CGC-TAT-TAC-GCC-AGC-TGG-CGA-AAG-GGG-GA-3' (SEQ ID NO:3)

Template polynucleotide

Bam HI digested M13mp7 or Phage DNA (Bethesda Research Labs (BRL), Gaithersburg, Md.), wherein M13mp7 was digested with Bam HI (BRL) according to protocol of manufacturer; M13mp19 RF from Pharmacia.
Other reagepts 10× Vent Buffer (100 mM KCL, 200 mM Tris-HCl, pH 8.8 at 25° C., 100 mM [NH$_4$]$_2$SO$_4$, 20 mM MgSO$_4$, 1% Triton X-100); Vent Polymerase (New England Biolabs, Beverly, Mass.); deoxyadenosine triphosphate (dATP), deoxyguanosine triphosphate (dGTP), deoxycytidine triphosphate (dCTP) and deoxythymidine triphosphate (dTTP) (referred to herein as dNTPs); H2O.

Method

Oligomers 1, 2 and 3 were synthesized by the phosphoramidite method using a Biosearch DNA synthesizer (Millipore Corpl, Bedford, Mass.) according to the manufacturer's protocol and were purified by polyacrylamide gel electrophoresis according to standard procedures. Concentrations were determined by absorbance at 260 nm. Oligomers were labelled at the 5' end with gamma-$^{32}$P-adenine triphosphate (ATP) by polynucleotide kinase. Typically, 5 pmoles of the oligomers was incubated with 50 pmoles of gamma-$^{32}$P-ATP and 5 units T4 polynucleotide kinase (Stratagene, San Diego, Calif.) for 1 h at 37° C. Unreacted triphosphate was removed by pa ssing the reaction mixture over a Push column (Stratagene, Inc., sold under the trademark NucTrap).

The reagents, except for the enzyme, were added (μl) in eppendorf tubes marked Nos. 1–11 as shown in Table I.

TABLE I

| Tube No. | 1 | 2 | 3 | 4 | 5 | 6 | 7 | 8 | 9 | 10 | 11 |
|---|---|---|---|---|---|---|---|---|---|---|---|
| H$_2$O | 13 | 13 | 13 | 12 | 12 | 12 | 7 | 7 | 7 | 5 | 5 |
| 10X Vent Buffer | 2 | 2 | 2 | 2 | 2 | 2 | 2 | 2 | 2 | 2 | 2 |
| dNTP's (2 mM) | 2 | 2 | 2 | 2 | 2 | 2 | 2 | 2 | 2 | 2 | 2 |
| M13mp7 0.4 pmoles/5 ml | — | — | — | — | — | — | 5 | 5 | 5 | 5 | 5 |
| Ext. Primer 0.125 pmoles/ml | 1 | — | — | 1 | — | — | 1 | — | — | 1 | 1 |
| 32P-Ext. Primer Tracer | 2 | — | — | 2 | — | — | 2 | — | — | 2 | 2 |
| GC Blocker 0.125 pmoles/ml | — | 1 | — | — | 1 | — | — | 1 | — | 2 | — |
| 32P-GC Block Tracer | — | 2 | — | — | 2 | — | — | 2 | — | — | — |
| AB Blocker 0.125 pmoles/ml | — | — | 1 | — | — | 1 | — | — | 1 | — | 2 |
| 32P-AB Block Tracer | — | — | 2 | — | — | 2 | — | — | 2 | — | — |
| Vent polymerase 1 unit/ml | 1 | 1 | 1 | 1 | — | — | 1 | 1 | 1 | 1 | 1 |

The above reaction mixtures were heated at 72° C. for 2 minutes and then were allowed to cool to the room temperature. After adding the enzyme to the tubes according to Table I, the reaction mixtures were incubated at 65° C. for 15 minutes. The reaction was stopped by adding 2 μl, 0.5M ethylenediaminetetraacetic acid (EDTA) solution and 2 μl of the reaction mixture from each tube was mixed with 4 μl of formamide dye mixture 1 (90% formamide, 0.2% bromophenol blue (BB), 0.2% xylene cyanol (XC)) and heated at 90° C. for 2 minutes and then cooled in ice.

The reaction products were evaluated by running 6 microlites of the formamide dye mixture on a 10% polyacrylamide, 8M urea gel, in 0.5 X Tris-borate-EDTA (45 mM Tris-borate (made from Tris-HCl and boric acid)/2 mm EDTA) (TBE) buffer and visualizing by exposure to X-ray film, a photocopy of which is shown in FIG. 8, which is discussed in more detail below. The yield of the products was determined by cutting out the bands and quantifying counts for each product.

Results and Discussion

The above reactions were carried out in order to demonstrate the method of the present invention to form a single stranded polynucleotide having two sequences that are non-contiguous and hybridizable with each other otherwise referred to as a stem loop structure. The method involved strand switching by an extending primer from a template polynucleotide to a polynucleotide Q in the presence of a blocker to form a polynucleotide with a stem loop structure. Polynucleotide Q, therefore, had a sequence S2 that was homologous to the extending primer.

The above reactions were carried out separately with one of two blocker polynucleotides: a GC Blocker (Oligomer 2) that hybridized to the template M13mp7 at bases 6351 to 6391 and an AB Blocker (Oligomer 3) that had (1) a sequence of 40 bases or nucleotides at its 3' end [-5'-GCG-GGC-CTC-TTC-GCT-ATT-ACG-CCA-GCT-GGC-GAA-AGG-GGG-A-3' (SEQ NO:4)] that was identical to a sequence in the GC Blocker and that was capable of binding to M13mp7 at the same location, and (2) a polynucleotide Q [5'-AGQ-CAT-GTT-TCG-GAA-CAC-CTA-TGC-TCC-CGC-ACC-GAT-CGC-C-3' (SEQ ID NO:5)] attached at its 5' end. Within Polynucleotide Q the 25 bases (underlined) at the 5' end were designated sequence S2, which was identical to 25 bases at the 5' end of the Ext. Primer (Oligomer 1). The remaining 15 bases were designated sequence S1. The 10 bases at the 3' end [-ACC-GAT-CGC-C- (SEQ ID NO:6)] of S1 were homologous to the 3' end of sequence T2, which was contiguous with the 3' end of sequence T3. The 5 bases [-CC-CGC-] at the 5' end of S1 were homologous to 5 bases at the 3' end of T3 and complementary to 5 bases at the 5' end of the AB Blocker.

Under the reaction conditions the Ext. Primer hybridized at bases 6441–6465 of the template and was extended along the template polynucleotide. As mentioned above, products obtained from the above reactions were visualized in the X-ray film of the polyacrylamide gel, a photocopy of which is shown in FIG. 8. The Lane Nos. shown in FIG. 8 correspond to the Tube Nos. of the above reactions with the exception of Tube Nos. 10–11, which correspond to Lane Nos. 11–12 and the sizes of marker DNA's are shown in Lane 10. In the absence of a blocker, Lane No.7, the product formed corresponded to the extension of the Ext. Primer to the end of the template (226 bases). In the presence of the GC Blocker (Lane No.11) approximately 40% of the products formed were about 100 bases in length (arising from the Ext. Primer stopping near the 5' end of the blocker), another 40% of the products formed were between 98–128 bases in length (arising from the extension of the Ext. Primer along a portion of the template to which the blocker was hybridized) and the remainder of the products formed were approximately 225 bases in length (arising from the complete displacement of the blocker from the template and extension of the Ext. Primer through the entire length of the template). In the presence of the AB Blocker (Lane No.12) no products were formed that were 100 bases in length; there was a prominent band, not observed in any other reaction, that corresponded to a product that was 137 bases in length (accounting for about 63% of the total products formed in this reaction No.12). This product of reaction No.12 corresponded to the predicted polynucleotide having a stem loop structure formed in accordance with the present invention.

In order to determine that the above 137 base product was indeed formed in accordance with the method of the present invention, the product was subjected to single primer amplification conditions and sequenced as discussed below.

Part B

Amplification of 137-Base Product

Materials

Single Primer 1
Oligomer 4 (25-mer)

5'-AGC-CAT-GTT-TCG-GAA-CAC-CTA-TGC-T-3'
(SEQ ID NO:7)

Single Primer 2
Oligomer 5 (25-mer)

5'-TGT-TGT-TCC-GTT-AGT-TCG-TTT-TAT-T-3' (SEQ ID NO:8)

Extender Primer No. 376 Sequence (56-mer)

5'-TGT-TGT-TCC-GTT-AGT-TCG-TTT-TAT-TGA-AAc-ACC-AGA-ACG-AGT-AGT-AAA-TTG-GGC-TT-3' (SEQ ID NO:9)

Oligomer 1 (Part A above)

Other reagents

10x Vent Buffer; reaction products #10 and #11 from
Part A; Vent Polymerase; dNTPs; H2O .

Method

Oligomers 4 and 5 were synthesized by the phosphoramidite method as described above and purified by polyacrylamide gel electrophoresis according to standard procedures. The reagents were added in the eppendorf tubes marked Nos. 1–8 as shown in Table II.

TABLE II

| Tube No. | 1 | 2 | 3 | 4 | 5 | 6 | 7 | 8 |
|---|---|---|---|---|---|---|---|---|
| Reaction Mixture # From Part A. Above | 11 | 11 | 11 | 11 | 10 | #10 | 10 | See below |
| Reaction amount (µl) | 2 | 4 | 8 | 4 | 2 | 4 | 8 | |
| H2O | 83 | 81 | 77 | 82 | 83 | 81 | 77 | |
| 10x Vent Buffer (µl) | 10 | 10 | 10 | 10 | 10 | 10 | 10 | |
| dNTP's (10 mM) (µl) | 2 | 2 | 2 | 2 | 2 | 2 | 2 | |
| Single Primer 1 Oligomer 4 (100 µM) (µl) | 1 | 1 | 1 | — | 1 | 1 | 1 | |
| Vent Polymerase (2 Units) (µl) | 2 | 2 | 2 | 2 | 2 | 2 | 2 | |

Tube Nos. 5–7 were negative controls and contained aliquots of reaction No.10 from Part A, above. These were not expected to have amplifiable DNA by single primer amplification. Tube No. 4 was a negative control as it contained no primer. Tube No. 8 was a positive control and contained H2O (83 µl), 10× Vent Buffer (10 µl), Extender Primer No. 376, 10 µM (1 µl), Single Primer 2 (Oligomer 5) (1 µl), (100 µM), 10 mMdNTP's (2 µl), M13mp19 template (1 µl, containing approximately 6×10$^6$ molecules) and Vent DNA polymerase (2 µl). Prior to adding the enzyme the reaction mixture in tube No. 8 was heated to 95° C. for 5 minutes and cooled at room temperature for 20 minutes. Thereafter, temperature cycling of 90° C. for 30 seconds, 55° C. for 60 seconds, and 72° C. for 90 seconds was performed using a programmable thermal cycler (Twin Block EZ Cycler, Ericomp, Inc., San Diego, Calif.) for a total number of 60 cycles through the 3 temperatures. 10 µl samples were drawn from various reaction mixture at 0 cycles (before adding the Vent DNA polymerase), 30 cycles and 60 cycles and mixed with 2 µl of 6X formamide dye mixture 2 (15% FICOLL 400, 0.25% BB, 0.25% XC dyes in H₂O). Accordingly, for example, Tube #1 was subjected to 0, 30 and 60 cycles respectively, which correspond to Lanes 1, 2 and 3, respectively, in FIG. 9.

The reaction products were evaluated by running the total 12 microlitres of the above samples on a 1% agarose, 3% Nusieve (FMC BioProducts, Rockford, Me.) agarose gel along side 5 µl of Biomarker (Bioventures, Inc., Murfreesboro, Tenn.) in 1X TBE buffer (containing 90 mM Tris-borate pH 8.3, 4 mM EDTA) and visualizing by staining the gel with 0.5 µg/ml of ethidium bromide solution.

Results and Discussion

As seen in the photocopy of the photograph of the above gel (FIG. 9), reaction No. 1 (Lane Nos. 1–3, with Lane 1 representing O cycles) yielded a product (designated as single primer amplification product) 130–140 bases in length after 30 cycles (Lane No. 2) and was present in considerable quantity after 60 cycles (Lane No. 3). Reaction Nos. corresponding to Lane Nos. 10–12, 14–16, 17–19 and 20–22, respectively, did not yield any amplified product as seen in Lane Nos. 4–7, respectively, and reaction No. 8 corresponding to Lane Nos. 23–25 yielded an amplified product approximately 183 bases in length as expected and as seen in Lane No.8. Lane Nos. 13 and 26 are molecular weight markers. Lanes Nos. 4–6 (Tube #2) and 7–9 (Tube #3) apparently resulted in SPA inhibition. Amplification of the product 130–140 bases in length by the single primer demonstrated that this product has an internal base paired structure or stem loop structure, which could only have been formed in accordance with the present invention. The above single primer amplification product was next purified and sequenced as described below.

Part C

Purification Step

Method

60 µl of the single primer amplification reaction mixture from above was mixed with 5 µl of 6X formamide dye mixture 2, described above, and 55 µl of this sample was loaded on and run on 3% NuSieve GTG agarose gel (FMC Bioproducts) in 40 mM Tris-acetate (made from Tris-HCl and acetic acid), 2 mM EDTA, pH 8.0 (TAE) buffer and visualized by staining with ethidiumbromide. The appropriate band was excised and placed in two-1.5 ml eppendorf tubes and purified using Mermaid kit (Bio 101) according to the manufacturer's directions for the removal of low molecular weight or oligomer DNA from the agarose gel. The purified DNA was suspended in 14 µl H2O .

Sequencing of Purified DNA: An Oligonucleotide Primer #10: 5'-CGC-TTC-TGG-TGC-CGG-AAA-CCA-GGC-A-3' (SEQ ID NO:10) was used together with a "Sequenase" kit (United States Biochemical Corp.) to sequence an aliquot of the purified product from above. Sequencing proved the identity of the product as an amplified DNA from the expected region of M13mp7 target polynucleotide.

Example 2

Synthesis of a Single Stranded Polynucleotide with Stem Loop Structure and its Amplification by Single Primer Amplification

Part A

Materials

Polynucleotide primer
Oligomer 6 (25-mer)

5'-CCC-GGT-TGA-TAA-TCA-GAA-AAG-CCC-C-3'
(SEQ ID NO:11)

Blocker polynucleotide with Polynucleotide Q attached (underlined portion) (Composite Blocker):
Oligomer 7 (80-mer)

5'-CCC-GGT-TGA-TAA-TCA-GAA-AAG-CCC-CCC-CGC-ACC-GAT-CGC-CGC-GGG-CCT-CTT-CGC-TAT-TAC-GCC-AGC-TGG-CGA-AAG-GGG-GA-3' (SEQ ID NO:12)

Master mix

Prepared by combining 10× Vent buffer (100 microliter, containing 20 mM Tris.HCl, pH 8.8, 100 mM KCl, 100 mM $(NH_4)_2SO_4$, 20 mM $MgSO_4$ and 1% Triton X-100), 20 mM dNTP (10 microliter), $10^{-4}$M primer (10 microliter), $10^{-7}$M blocker (10 microliter) and $H_2O$ (670 microliter) for a total of 800 microliter.

Template polynucleotide

Linearized single stranded (s.s) M13mp7 and double stranded (d.s) M13mp19

METHOD

Oligomers 6 and 7 were synthesized by the phosphoramidite method referred to above and purified on denaturing polyacrylamide gels according to standard procedures. Polynucleotide Q was the 40–5' terminal bases [5'-CCC-GGT-TGA-TAA-TCA-GAA-AAG-CCC-CCC-CGC-ACC-GAT-CGC-C- (SEQ ID NO:14)] of Oligomer 7 and was attached to the 5' end of the blocker polynucleotide, which was the 40–3' terminal bases [-GC-GGG-CCT-CTT-CGC-TAT-TAC-GCC-AGC-TGG-CGA-AAG-GGG-GA-3' (SEQ ID NO:14)] of Oligomer 7. Within Polynucleotide Q the 25-5' terminal bases (underlined) were designated as sequence S2, which was identical to polydeoxynucleotide primer Oligomer 6, and the remaining 15 bases at the 3' end of polynucleotide Q were designated as sequence S1 wherein the 5' end of S1 consists of 5 bases [-CC-CGC- (SEQ ID NO:16)] complementary to the 5 bases at the 5' end of the blocker polynucleotide and the 3' end of S1 consists of 10 bases [-ACC-GAT-CGC-C- (SEQ ID NO:17)] that were homologous to bases 6391–6400 on the template polynucleotide. The Composite Blocker was capable of hybridizing to M13mp7 at bases 6351–6390. Extension of the polynucleotide primer in accordance with the present invention generated an amplifiable polynucleotide sequence having an intramolecular base pair structure or stem loop structure. The polynucleotide primer hybridized to M13mp7 at bases 6806–6830.

The formation and amplication of such a stem loop molecule was carried out using single stranded M13mp7 and M13mp19 (double-stranded replicarive form, 7250 base pairs from Bethesda Research Laboratories). Both were linearized by digestion with Bam HI according to manufacturer's directions to give template polynucleotide and M13mp19 was further denatured by heating it in boiling water for 10 minutes and immediately putting it in ice water before carrying out further steps. 80 microlitres of the master mix was added to eppendorf tubes marked Nos. 1–9 containing varying amounts of the template polynucleotides (Table III), and the above reaction mixtures were heated at 94° C. for 4 minutes and cooled to room temperature for 10 minutes. This allowed the primer and the extended blocker to anneal to the template polynucleotide. Pfu polymerase (Stratagene, Inc.) was added (5 units). Temperature cycling of 90° C. for 30 seconds, 55° C. for 60 seconds and 72° C. for 90 seconds was performed using a programmable thermal cycler (Ericomp, Inc.) for a total number of 60 cycles through the 3 temperatures. Products of the amplification were evaluated by running 15 microlitres of the reaction media along side appropriate controls on a 1.2% agarose gel, in 0.5× TBE buffer and visualizing by staining the gel with ethidium bromide; a photocopy of the photograph of the gel is shown in FIG. 10. Lane Nos. 1–9 correspond to Tube Nos. 1–9, Lane No. 10 is s.s M13mp7 as a positive control, Lane No. 11 is d.s M13mp19 as a positive control and Lane No. 12 is a negative control and Lane No. 13 represents molecular weight markers.

TABLE III

| Tube No. | Template conc. (molecules) |
|---|---|
| 1 | $10^2$ s.s M13mp7 |
| 2 | $10^4$ s.s M13mp7 |
| 3 | $10^6$ s.s M13mp7 |
| 4 | $10^8$ s.s M13mp7 |
| 5 | $10^2$ d.s M13mp19 |
| 6 | $10^4$ d.s M13mp19 |
| 7 | $10^6$ d.s M13mp19 |
| 8 | $10^8$ d.s M13mp19 |
| 9 | 10 d.s M13mp19 |

Part B

The above experiment was repeated with circular double stranded (d.s) M13mp19 as the template polynucleotide at different concentrations (see Table IV). The products of the amplification were evaluated by running 15 microliter of each of the reaction mixtures alongside appropriate controls on a 1.2 % agarose gel, in 0.5× TBE buffer and visualizing by staining the gel with ethidiumbromide (See FIG. 11, discussed in more detail below, wherein Lane Nos. 1 and 9 correspond to molecular weight markers, Lane Nos. 2–5 correspond to Tube Nos. 1–4. Lane Nos. 6–8 had nothing loaded and Lane No.7 was a negative control having no target.)

TABLE IV

| Tube No. | Template Conc. (molecules |
|---|---|
| 1 | $10^2$ d.s M13mp19 |
| 2 | $10^3$ d.s M13mp19 |
| 3 | $10^4$ d.s M13mp19 |
| 4 | $10^5$ d.s M13mp19 |

RESULTS AND DISCUSSION

The formation and amplification of a polynucleotide product 450 bases in length as indicated in FIGS. 10 and 11 demonstrates that the polynucleotide primer (Oligomer 6) was extended along the template polynucleotide up to the Composite Blocker before it switched strands and was extended along polynucleotide Q to give extended primer having an internal base paired structure or stem loop structure. The latter molecule was then amplified by single primer amplification as described earlier.

Example 3

Effect of Temperature on Formation of a Single Stranded Polynucleotide Having a Stem Loop Structure Materials Polynucleotide primer with and without $^{32}$P label (Primer and Tracer Primer, respectively):
Oligomer 8 (25-mer)

5'-CCC-GGT-TGA-TAA-TCA-GAA-AAG-CCC-C-3' (SEQ ID NO:16) Extended Blocker (having Polyneocleotide O) with and without $^{32}$P label:

Oligomer 9 (80-mer)

5'-CCC-GGT-TGA-TAA-TCA-GAA-AAG-CCC-CCC-CGC-ACC-GAT-CGC-CGC-GGG-CCT-CTT-CGC-TAT-TAC-GCC-AGC-TGG-CGA-AAG-GGG-GA-3' (SEQ ID NO:17) Template polynucleotide (Template):

Bam HI digested M13mp7 single stranded phage DNA
Others reagents
10× Vent Buffer, Pfu Polymerase; dNTPs; H2O.
Method Oligomers 8 and 9 were synthesized by the phosphoramidite method described above and purified by polyacrylamide gel electrophoresis according to standard procedures. The Extended Blocker (Oligomer 9), was capable of hybridizing to M13mp7 at bases 6351–6390. The polynucleotide primer (Oligomer 8) served to generate an amplifiable polynucleotide sequence having an intramolecular base pair, or stem loop, structure and hybridized to M13mp7 at bases 6806–6830. All the reagents except for the enzyme were added (µl) in eppendorf tubes marked Nos. 1–6 as shown in Table V.

TABLE V

| Tube No. | 1 | 2 | 3 | 4 | 5 | 6 |
|---|---|---|---|---|---|---|
| H$_2$O (µl) | 10 | 9 | 9 | 9 | 9 | 9 |
| 10X Vent Buffer (µl) | 2 | 2 | 2 | 2 | 2 | 2 |
| 2 mM dNTP's (µl) | 2 | 2 | 2 | 2 | 2 | 2 |
| 0.25 pmoles/3 µl M13mp7 Template (µl) | 3 | 3 | 3 | 3 | 3 | 3 |
| 0.25 pmoles/µl Oligomer 9 Extended Blocker (µl) | 1 | 1 | 1 | 1 | 1 | 1 |
| 0.25 pmoles/µl Oligomer 8 Primer (µl) | 1 | 1 | 1 | 1 | 1 | 1 |
| 32P Tracer Oligomer 8 Primer (µl) | 2 | 2 | 2 | 2 | 2 | 2 |
| 2.5 Units/µl Pfu DNA Polymerase | 1 | 1 | 1 | 1 | 1 | 1 |
| Temp. (°C.) of Extension Reaction | 65 | 55 | 60 | 65 | 70 | 75 |

The above reaction mixtures were heated at 94° C. for 4 minutes and then allowed to cool to the room temperature. After adding the enzyme to the tubes according to Table V the reaction mixtures were incubated at indicated temperatures for 15 minutes. 2 µl of the reaction mixture from each tube was mixed with 4 µl of formamide dye mixture 2, described above, and heated at 94° C. for 4 minutes and then cooled in ice.

The reaction products were evaluated by running 6 microlites of the aliquots plus formamide dye mixture on a 6% acrylamide, 8M urea gel, in 0.5×TBE buffer and visualizing by exposure to X-ray film, a photocopy of which is shown in FIG. 12, which is discussed in more detail below.

Results and Discussion

In order to determine the effect of temperature on strand switching resulting in the formation of a polynucleotide with a stem loop structure, the above reaction was conducted. The reaction was done with the extended blocker. The Extended Blocker had 40 bases at the 3' end capable of hybridizing to the template. The 40 bases at the 5' end of the Extended Blocker comprised polynucleotide Q. Within polynucleotide Q the 25 bases at its 5' end were the same as the primer.

The products obtained from the above reactions at different temperatures with the Extended Blocker are shown in the photocopy of the X-ray film of the gel (FIG. 12). Lanes 2–7 correspond to reaction nos. 1–6 and Lane 1 indicates the sizes of marker DNA's. In the absence of a blocker reaction no. 1 (Lane 2) the product corresponded to the extension of the primer to the end of the template (566 bases). However, as the temperature increased (Lanes 3–6) there was an increase in the amount of the expected strand switched product of approximately 480 bases in length (arrows on FIG. 12). At 75° C., when polymerase was efficiently displacing blocker oligomer 8 (Lane 7), the amount of this expected product decreased.

Example 4

Synthesis of a Single Stranded Polynucleotide with Stem Loop Structure Upon E. coli Genomic DNA and its Amplification by Single Primer Amplification Part A Materials Polynucleotide Primer
Oligomer 10 (25-mer)

5-CAA-AAC-AGC-GGA-AGA-GCG-TGA-AAT-C-3, (SEQ ID NO:18)

Blocker Polynucleotide with Polynucleotide O (underlined) Attached (Composite Blocker):
Oligomer 11 (80-mer)

5'-CAA-AAC-AGC-GGA-AGA-GCG-TGA-AAT-CGG-CCC-TGA-CAG-TGT-GGG-GCC-GCG-GTA-CGC-TGA-TCA-AAG-ATC-CGT-GCA-ACA-AAT-GT-3' (SEQ ID NO:19)

Standard Reaction Mix (100 microliters) Prepared by combining 9 microliters of 10× Pfu buffer #2 (containing 200 mm TRIS-Cl, pH 8.8 (25° C.), 100 mM KCl, 60 mM (NH$_4$)$_2$SO$_4$, 15 mM MgCl$_2$, 1% TRITON X-100), 1 microliter of 20 mM dNTP's, 0.5 microliter of 2×10$^{-4}$M Oligomer 10, 0.5 microliter of 2×10$^{-5}$M Oligomer 11, 2 microliters of 2.5 units/microliter Pfu DNA Polymerase (Strategene, Inc.), E. coli genomic DNA target in 10 microliters 1X Pfu buffer #2, and water to make a final volume of 100 microliters.

Method 15 reactions of 100 microliters volume each were tested for amplification yields. Two components of the reactions were varied. The E. coli genomic DNA target concentrations were, in groups of five reactions, 10$^6$, 10$^4$, 10$^2$, 10 and 0 targets, respectively, per test tube.

This group of five reactions was made in quadruplicate, and the resulting four sets of five reactions were each treated with a different temperature cycling protocol. All reactions were assembled at room temperature, and then cycled once at 96° C. for 5 mins., 65° C. for 10 mins. and 72° C. for 4 mins. Then, the first set of five reactions was cycled 60 times at 93° C. 1 min., 63° C. 1 min. and 72° C. 1.5 mins. In the next three sets of reactions the lowest annealing temperature was raised 2° C. for each set, e.g., 65° C. for the second set of five reactions, 67° C. for the third, and 69° C. for the fourth. The extension time at these temperatures remained 1 minute. The purpose of these experiments was to study optimization protocols for SPA on bacterial genomic targets.

FIG. 13 is a photocopy of an agarose gel electrophoresis of aliquots of nineteen single primer amplification reactions described above. Lanes 1–5 are single primer amplification reactions with 10$^6$, 10$^4$, 10$^2$, 10 and 0 targets where the lowest annealing temperature in the 60 cycles was 63° C. Lanes 6–10, 11–15 and 16–19 represent the remaining three sets of five reactions in the same series of target number but with annealing temperatures of 65° C., 67° C. and 69° C. respectively. The 0 target reaction of the fourth set is not shown. A size marker is in Lane 20.

Results and Discussion

The expected size of the single primer amplified DNA product is indicated by an arrow in FIG. 13. This designation was verified by restriction enzyme digestion of the product and hybridization to appropriate probes (data not shown). FIG. 13 shows that, as the lowest annealing temperature rose above 65° C., the sensitivity of this series of single primer amplification reactions began to decrease. The best temperature regimen for this target, with the above primer and blocker combination and under the above buffer conditions, appears to be 93° C. 1 min., 65° C. 1 min. and 72° C. 1.5 mins. Amplified DNA representing amplification from 10 targets of DNA is clearly visible in Lane 9. All negative target controls on this gel, Lanes 5, 10, and 15, show no amplified target, as expected. Lane 20 is a size marker (50–1000 bp from Research Genetics).

Example 5

Synthesis of a Single Stranded Polynucleotide with Stem Loop Structure Upon Mycobacterium tuberculosis Genomic DNA in the presence of Human Genomic DNA and its Amplification by Single Primer Amplification Materials
Polynucleotide primer
Oligomer 12 (25-mer)
    5'-TAG-CCC-TTG-TCG-AAC-CGC-ATA-CCC-T-3'
    (Seq ID No:20)
Blocker Polynucleotide with Polynucleotide O (underlined) Attached (Composite Blocker):
Oligomer 13 (70-mer)
    5'-TAG-CCC-TTG-TCG-AAC-CGC-ATA-CCC-TGT-
    GTG-TCC-ATA-TGG-ACA-CAC-CAT-CGT-TGG-
    TGA-TCG-TGG-GGG-CAC-C -3' (Seq. ID No. 21)
Standard Reaction Mix
(100 microliters) Prepared by combining 10 microliters of 10X Pfu buffer (containing 100 mM TRIS-HCl, pH 8.8 (25° C.), 500 mM KCl, 15 mM MgCl$_2$, 1% TRITON X-100, 75 mM Dithiothreitol, 2 microliters of 10mM dNTP's, 1 microliter of 100 µM Oligomer 12, 1 microliter of 5 µM Oligomer 13, 2 microliters of 2.5 units/microliter cloned Pfu polymerase (Stratagene, Inc.), varying amounts of M. tuberculosis genomic DNA and varying amounts of total human placental genomic DNA (SIGMA), and water to make a total volume of 100 microliters.
Method
Fifteen (15) separate amplification reactions were prepared in which their were three sets of five which had approximately $10^4$, $10^3$, $10^2$, 10 and 0 molecules of M. tuberculosis genomic DNA in each of the five tubes, respectively. The first set of five had no added human genomic DNA, the second set of five had 10 ng. of human genomic DNA and the third set of five had 100 ng. of human genomic DNA added. The reactions were assembled at room temperature (approximately 22° C.) then denatured at 95° C. for 3 minutes, and then temperature cycled using 45 cycles consisting of the three temperature regimen: 94° C. for 1 minute, 66° C. for 1 minute , and 72° C. for 1 minute.

FIG. 14 is a picture of an ethidium bromide stained 1.2% agarose gel onto which has been run 12 microliters of the 100 microliters from the above 15 temperature cycled reactions. The expected size amplicon (450 base pairs) is detectable in all reactions containing M. tuberculosis genomic target DNA, except for the reaction containing approximately 10 targets in the presence of 100 ng. of human genomic DNA (lane 15 of FIG. 14).

In order to suppress mispriming and thereby achieve more specific and sensitive amplification of the M. tuberculosis target DNA, reactions similar to those above were assembled at 72° C. before temperature cycling was begun. Specifically, 50 microliters consisting of 400 µM dNTP's, 2 µM primer oligomer 12, 100 nM blocker oligomer 14, and water all in 1X buffer was heated to 72° C. Another 50 microliter volume consisting of 5 units of PfU DNA polymerase, 1 microgram of human placental genomic DNA, varying concentrations of M. tuberculosis genomic DNA and water all in 1X buffer was heated to 72° C. These two volumes were mixed rapidly in order to form a complete reaction of 100 microliters which maintains a temperature above 66° C. The reaction was denatured for 3 minutes at 95° C., then temperature cycled through a three temperature regimen of 94° C. for 1 minute, 66° C. for 1 minute and 72° C. for 1 minute.

Twelve (12) microliter aliquots of the above reactions were examined on agarose gels as above, except that aliquots were withdrawn at 45, 50, 55 and 60 temperature cycles (FIG. 15). Unlike in the first set of reactions above, these set of reactions which incorporate starting the reactions at a high temperature and which contain 1 microgram of human genomic DNA allowed detection of approximately 10 molecules of M. tuberculosis genomic DNA targets (see lanes 5, 10,15 and 20 of FIG. 15). The expected amplicon band of 450 base pairs is indisputable in the 10 target, 60 cycle lane. The bands seen in the gel of the negative controls (0 targets) are nonspecific amplifications (lanes 6, 11, 16 and 21). This interpretation is supported by restriction digestion mapping of the amplified DNA's (FIG. 16). The expected restriction fragments from the 450 bp ampiicons were present in digests of all amplifications except the 0 target controls.

A comparison of Single Primer Amplification to the Polymerase chain Reaction (PCR), performed using the same target genomic DNA of M. tuberculosis, showed equal sensitivity, but the PCR gave an intensely staining band often referred to as a "primer-dimer" which was not present in the SPA reactions.
Results and Discussion
It is desirable that a DNA amplification technique be capable of amplifying small numbers of target molecules despite the presence of vast excess of non-target DNA molecules. Clinical samples containing the DNA target of interest will often contain large amounts of non-target DNA, and the amplification must be specific enough to detect only target and amplify little or none of non-target DNA. The SPA primer and blocker used in this example were directed to a region of genomic DNA known to be generic for various species of mycobacteria (Journal of Clinical Microbiology (1993), Vol. 31, No. 2, pp. 175–178. "Rapid Identification of Mycobacteria to the Species Level by Polymerase chain Reaction and Restriction Enzyme Analysis."). This example demonstrates the ability of Single Primer Amplification to amplify small numbers Mycobacterial genomic DNA in the presence of vast excess human DNA.
FIG. 14
Non "hot-start" SPA reaction with added human genomic DNA.
Lanes 1 and 17 contained a DNA size ladder standard of 123 base pair (bp) (BRL, Inc.). Lanes 2–6, 7–11 and 12–16 were aliquots of reactions containing $10^4$, $10^3$, $10^2$, 10 and 0 molecules of M. tuberculosis (M. tb.) genomic DNA target present in the SPA reactions described in the text. The group of reactions 2–6 had no added human genomic DNA. Reactions 7–11 contained 10 nanograms of human genomic DNA and reactions 12–16 contain 100 nanograms of genomic DNA. The expected 450 base pair amplicon band of SPA from lane 15 was lost in this series of reactions, presumably due to loss of sensitivity when competing human genomic DNA was present in this non "hot-start" reaction of only 10 targets of *M. tb.* genomic DNA.

FIG. 15

"Hot-start" SPA reactions with 1 microgram of human genomic DNA added.

Lanes 1 and 22 contained the 123 bp standard DNA ladder. Lanes 2–6, 7–11, 12–16, and 17–21 represented aliquots from reactions containing $10^4$, $10^3$, $10^2$, 10 and 0 targets of *M. tb.* genomic DNA. Lanes 2–6 represented the reactions after 45 temperature cycles; lanes 7–11 after 50 cycles; lanes 12–16 after 55 temperature cycles and lanes 17–21 after 60 temperature cycles. All five reactions contained 1 microgram of human placental genomic DNA. Even with as few as 10 target *M. tb* genomes, the original photograph demonstrated detection of the expected 450 bp amplicon in as few as 45 cycles (lane 5). No 450 bp bands were detected in this agarose gel in the 0 target negative controls (lanes 6, 11, 16 and 21).

FIG. 16

Restriction enzyme analysis of selected SPA and PCR reaction amplicon products.

Lanes 1 and 12 were DNA size markers: lane 1 was an Msp 1 digest of pBR322 and lane 12 was a 123 bp ladder (BRL, Inc). All products on this gel come from SPA (FIG. 15) or PCR reactions. Lanes 2 and 3 represented before and after BstE II restrictions digests of the SPA amplicon from 100 targets of *M tb.* DNA, after 60 cycles of amplification.

The expected restriction fragments of 245, 125 and 80 base pairs were detectable in lane 3, proving the identity of the 450 bp amplicon from lane 2. Lanes 4 and 5 represented digestion of the 450 bp amplicon from a SPA using 10 targets. Lane 5 again showed the faint but detectable expected BstE II restriction pattern, as well as nonspecific amplification products which are not substrates for BstE II. Lanes 6 and 7 were a similar study where no *M. tb.* targets were present, and there was no detectable 450 bp amplicon nor restriction products from this ampiicon. Lanes 8 and 9 represented the 440 bp amplicon from a PCR reaction using 100 targets after 60 cycles. BstE II restriction enzyme treatment yielded the expected 235, 125, and 80 bp fragments. Lanes 10 and 11 were the same as 8 and 9 except the PCR started with 10 targets. The expected amplicon and restriction fragment were present.

The above discussion includes certain theories as to mechanisms involved in the present invention. These theories should not be construed to limit the present invention in any way, since it has been demonstrated that the present invention achieves the results described.

The above description and examples disclose the invention including certain preferred embodiments thereof. Modifications of the methods described that are obvious to those of ordinary skill in the art such as molecular biology and related sciences are intended to be within the scope of the following claims and included within the metes and bounds of the invention.

What is claimed is:

1. A method for producing a single stranded polynucleotide having two or more defined nucleic acid sequences, said method comprising the steps of:

(a) hybridizing a sequence B1 of a blocker polynucleotide to a complementary sequence T3 within a template polynucleotide ("template"), said template being comprised of a sequence T1 and a sequence T2, wherein the 5' end of said T3 is 5' of the 5' end of said T2 and said T2 and T3 are 5' to and non-contiguous with said sequence T1, (b) hybridizing the 3' end of a polynucleotide primer comprising a second defined nucleic acid sequence to said T1 wherein step (b) is performed prior to, after, or simultaneously with step (a), and (c) extending said primer, by means of a polymermase, along said template and along at least a portion of said T2 and thereafter along a polynucleotide Q having sequences S1 and S2 wherein S1 is 3' of S2 and substantially identical with said T2 to give an extended primer having a first defined nucleic acid sequence at its 3' end that is complementary to S2, wherein polynucleotide Q is either attached to the 5' end of said blocker polynucleotide or is present as a separate reagent, wherein said polymerase has little or no 5'-3' exonuclease activity during said extending, and wherein the 3'-end of said polynucleotide Q, when present as a separate reagent, is not extended by said polymerase during said extending.

2. A method for producing from a primer polynucleotide a single stranded polydeoxynucleotide having two segments that are non-contiguous and complementary with each other, said method comprising the steps of:

(a) providing in combination (a) a template polynucleotide having three sequences T1, T2 and T3 wherein T1 is non-contiguous and 3' of said T2 and T3 and the 3' end of said T3 is oontiguous with or lies within said T2, (b) a pdmer polynucleotide whose 3' end is hybridizable with said T1 (c) a blocker polynucleotide with sequence B1, said B1 being hybridizable with said T3, and (d) a polynucleotide Q having sequence S1 and sequence S2 wherein said Q is either attached to the 5' end of said blocker polynucleotide or present as a separate reagent and wherein S1 is 3' of said S2 and substantially identical to said T2 and wherein said S2 is a sequence that is substantially identical to at least the 3' end of said pdmer polynucleotide, and (b) subjecting said combination to conditions for extending said primer, by means of a polymerase, along said template polynucleotide and along at least a portion of said T2, and thereafter along said polynucleotide Q, wherein said polymerase has little or no 5'-3' exonuclease activity under said conditions for extending, and wherein the 3'-end of said polynucleotide Q, when present as a separate reagent, is not extended during said extending.

3. The method of claim 2 wherein at least a five base sequence within said B1 is comprised of at least 80% G and C nucleotides.

4. The method of claim 2 wherein said S1 is from 5 to 50 nucleotides in length.

5. The method of claim 2 wherein a sequence comprising the 5' end of said S1 is complementary to a sequence comprising the 5' end of said B1.

6. The method of claim 2 wherein the 5' end of said S1 is not complementary to the 5' end of said B1.

7. The method of claim 2 wherein said T2 is contiguous with said T3.

8. The method of claim 2 wherein the 3'-end of said polynucleotide Q is attached to the 5' end of said blocker polynucleotide.

9. A method of producing at least one copy of a target polynuoleotide sequence, said method comprising the step of:

providing in combination (1) a template polynucleotide having three sequences T1, T2 and T3 wherein T1 is non-contiguous and 3' of said T2 and T3 and wherein the 3' end of said T3 is contiguous with or lies within said T2 and wherein said target polynucleotide sequence is located between said T1 and T3, (2) a primer polynucleotide whose 3' end is hybridizable with said T1, (3) a blocker polynucleotide with sequence B1, said B1 being hybridizable with said T3, (4) a polynucleotide Q having sequences S1 and S2 wherein said Q is either attached to the 5' end of said blocker polynucleotide or present as a separate reagent and wherein S1 is 3' of S2 and substantially identical to said T2 and wherein said S2 is a sequence that is substantially identical to at least the 3' end of said primer polynucleotide, (5) DNA polymerase and (6) deoxynucleoside triphosphates under conditions wherein: (A) said blocker becomes hybridized to said template polynucleotide, (B) said primer becomes hybridized with and extended along said target polynucleotide sequence of said template polynucleotide and along at least a portion of said T2, and thereafter along said polynucleotide Q to form a duplex, (C) said extended primer is dissociated from the said duplex, and (D) said primer hybridizes with and is extended along said extended primer to form a duplex comprising extended primer containing a copy of said target sequence, wherein the 3'-end of said polynucleotide Q, when present as a separate reageent, is not extended by said DNA polymerase.

10. The method of claim 9 which comprises the step of examining for the presence of said extended primer.

11. The method of claim 9 wherein at least a five base sequence of B1 is comprised of at least 80% G and C nucleotides.

12. The method of claim 9 wherein said S1 is from 5 to 50 nucleotides in length.

13. The method of claim 9 wherein a sequence comprising the 5' end of said S1 is complementary to a sequence comprising the 5' end of said B1.

14. The method of claim 9 wherein the 5' end of said S1 is not complementary to the 5' end of said B1.

15. The method of claim 9 wherein said T2 is contiguous with said T3.

16. The method of claim 9 wherein steps (C) and (D) are repeated.

17. The method of claim 9 wherein the 3'-end of said polynucleotide Q is attached to the 5' end of said blocker polynucleotide.

18. A method of forming multiple copies of a target polynucleotide sequence, said method comprising the steps of:

(a) providing in combination (1) a template polynucleotide having three sequences T1, T2 and T3 wherein T1 is non-oontiguous and 3' of said T2 and T3 and wherein the 3' end of said T3 is contiguous with or lies within said T2 and wherein said target polynucleotide sequence is located between said T1 and T3, (2) a primer polynucleotide whose 3' end is hybridizable with said T1, (3) a blocker polynucleotlde with sequence B1, said B1 being hybridizable with said T3, (4) a poly-nucleotide Q having sequences S1 and S2 wherein said Q is either attached to the 5' end of said blocker polynucleotide or present as a separate reagent and wherein S1 is 3' of S2 and substantially identical to said T2 and wherein said S2 is a sequence that is substantially identical to at least the 3' end of said primer polynucleotide, (5) DNA polymerase and (6) deoxynucleoside triphosphates under conditions wherein: (A) said blocker becomes hybridized to said template polynucleotide, (B) said primer becomes hybridized with and extended along said target polynucleotide sequence of said template polynucleotide and along at least a portion of said T2 and thereafter along said polynucleotide Q to form a duplex, (C) said extended primer is dissociated from the said duplex, and (D) said primer hybridizes with and is extended along said extended primer to form a duplex comprising extended primer containing a copy of said target sequence, wherein the 3'-end of said polynuoleotide Q, when present as a separate reagent, is not extended by said DNA polymerase and (b) repeating steps (C) and (D).

19. The method of claim 18 which comprises examining for the presence of said extended primer.

20. The method of claim 18 wherein at least a five base sequence said B1 is comprised of at least 80% G and C nucleotides.

21. The method of claim 18 wherein said S1 is from 5 to 50 nucleotides in length.

22. The method of claim 18 wherein a sequence comprising the 5' end of said S1 is complementary to a sequence comprising the 5' end of said B1.

23. The method of claim 18 wherein the 5' end of S1 is not complementary to the 5' end of said B1.

24. The method of claim 18 wherein said T2 is contiguous with said T3.

25. The method of claim 18 wherein the 3'-end of said polynucleotide Q is attached to the 5' end of said blocker polynucleotide.

26. A method of forming multiple copies of a target polynucleotide sequence, said method comprising the steps of:

(a) providing in combination (1) a template polynucleotide having three sequences T1, T2 and T3 wherein T1 is non-contiguous and 3' of said T2 and T3 and wherein the 5' end of said T3 is 5' of the 5' end of said T2 and wherein said target polynucleotide sequenoe is located between said T1 and T3, (2) a primer polynucleotide whose 3' end is hybridizable with said T1, (3) a blocker polynucleotide with sequence B1, said B1 being hybridizable with said T3, (4) a polynucleotide Q having sequences S1 and S2 wherein the 3'-end of said Q is attached to the 5' end of said blocker polynucleotide and wherein S1 is 3' of S2 and substantially identical to said T2 and wherein said S2 is a sequence that is substantially identical to at least the 3' end of said primer polynucleotide, (5) DNA polymerase and (6) deoxynucleoside triphosphates under conditions wherein: (A) said blocker becomes hybridized to said template polynucleotide, (B) said primer becomes hybridized with and extended along said target polynucleotide sequence of said template polynucleotide and along at least a portion of said T2 and thereafter along said polynucleotide Q to form a duplex, (C) said extended primer is dissociated from the said duplex, and (D) said primer hybridizes with and is extended along said extended primer to form a duplex comprising extended primer containing a copy of said target sequence, and (b) repeating steps (C) and (D).

27. The method of claim 26 which comprises examining for the presence of said extended primer.

28. The method of claim 26 wherein at least a five base sequence said B1 is comprised of at least 80% G and C nucleotides.

29. The method of claim 26 wherein said S1 is from 5 to 50 nucleotides in length.

30. The method of claim 26 wherein the 5' end of said S1 is complementary to the 5' end of said B1.

31. The method of claim 26 wherein the 5' end of said S1 is not complementary to the 5' end of said B1.

32. The method of claim 26 wherein said T2 is contiguous with said T3.

33. The method of claim 26 wherein said T2 is not contigous with said T3.

34. A kit comprising in packaged combination:
 (a) a primer polynucleotide having a sequence at its 3' end hybridizable with a first sequence T1 in a target polynucleotide
 (b) a blocker polynucleotide having a sequence B1, said B1 being hybridizable with a sequence T3 in said target polynucleotide wherein said T3 is 3' of said T1 and the 5' end of said T3 is 5' of the 5' end of a sequence T2, and
 (c) a polynucleotide Q having sequences S1 and S2 wherein S1 is 3' of said S2 and substantially identical to said T2 in said template polynucleotide and wherein said S2 is a sequence that is substantially identical to at least the 3' end portion of said primer.

35. The kit of claim 34 wherein said polynucleotide Q is a part of said blocker polynucleotide.

36. The kit of claim 34 wherein said polynucleotide Q is separate from said blocker polynucleotide.

37. The kit of claim 34 which comprises template dependent DNA polymerase.

38. The kit of claim 34 which comprises deoxynucleoside triphosphates.

39. The kit of claim 34 wherein said primer is labeled with a reporter molecule.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( v i ) ORIGINAL SOURCE:
        ( A ) ORGANISM: synthetic ( x i ) SEQUENCE DESCRIPTION: SEQ ID NO:1:

```
AGCCATGTTT  CGGAACACCT  ATGCTCGCTT  CTGGTGCCGG  AAACCAGGCA                    50
```

( 2 ) INFORMATION FOR SEQ ID NO:2:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO (i v) ANTI-SENSE: NO (v) FRAGMENT TYPE: internal (v i) ORIGINAL SOURCE:
    (A) ORGANISM: synthetic (x i) SEQUENCE DESCRIPTION: SEQ ID NO:2:

GCGGGCCTCT TCGCTATTAC GCCAGCTGGC GAAAGGGGGA 40

(2) INFORMATION FOR SEQ ID NO:3:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (v) FRAGMENT TYPE: internal (v i) ORIGINAL SOURCE:
        (A) ORGANISM: synthetic (x i) SEQUENCE DESCRIPTION: SEQ ID NO:3:

AGCCATGTTT CGGAACACCT ATGCTCCCGC ACCGATCGCC GCGGGCCTCT TCGCTATTAC 60

GCCAGCTGGC GAAAGGGGGA 80

(2) INFORMATION FOR SEQ ID NO:4:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (v) FRAGMENT TYPE: internal (v i) ORIGINAL SOURCE:
        (A) ORGANISM: synthetic (x i) SEQUENCE DESCRIPTION: SEQ ID NO:4:

GCGGGCCTCT TCGCTATTAC GCCAGCTGGC GAAAGGGGGA 40

(2) INFORMATION FOR SEQ ID NO:5:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (v) FRAGMENT TYPE: internal (v i) ORIGINAL SOURCE:

( A ) ORGANISM: synthetic ( x i ) SEQUENCE DESCRIPTION: SEQ ID NO:5:

AGCCATGTTT CGGAACACCT ATGCTCCCGC ACCGATCGCC 40

( 2 ) INFORMATION FOR SEQ ID NO:6:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( v i ) ORIGINAL SOURCE:
        ( A ) ORGANISM: synthetic ( x i ) SEQUENCE DESCRIPTION: SEQ ID NO:6:

ACCGATCGCC 10

( 2 ) INFORMATION FOR SEQ ID NO:7:

( i ) SEQUENCE CHARACTERISTICS:
        ( A ) LENGTH: 5 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( v i ) ORIGINAL SOURCE:
        ( A ) ORGANISM: synthetic ( x i ) SEQUENCE DESCRIPTION: SEQ ID NO:7:

CCCGC 5

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( v i ) ORIGINAL SOURCE:
        ( A ) ORGANISM: synthetic ( x i ) SEQUENCE DESCRIPTION: SEQ ID NO:8:

AGCCATGTTT CGGAACACCT ATGCT 25

( 2 ) INFORMATION FOR SEQ ID NO:9:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( v i ) ORIGINAL SOURCE:
    ( A ) ORGANISM: synthetic ( x i ) SEQUENCE DESCRIPTION: SEQ ID NO:9:

TGTTGTTCCG TTAGTTCGTT TTATT                        25

( 2 ) INFORMATION FOR SEQ ID NO:10:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( v i ) ORIGINAL SOURCE:
        ( A ) ORGANISM: synthetic ( x i ) SEQUENCE DESCRIPTION: SEQ ID NO:10:

TGTTGTTCCG TTAGTTCGTT TTATTGAAAC ACCAGAACGA GTAGTAAATT GGGCTT    56

( 2 ) INFORMATION FOR SEQ ID NO:11:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( v i ) ORIGINAL SOURCE:
        ( A ) ORGANISM: synthetic ( x i ) SEQUENCE DESCRIPTION: SEQ ID NO:11:

CGCTTCTGGT GCCGGAAACC AGGCA                        25

( 2 ) INFORMATION FOR SEQ ID NO:12:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( v i ) ORIGINAL SOURCE:
    ( A ) ORGANISM: synthetic ( x i ) SEQUENCE DESCRIPTION: SEQ ID NO:12:

CCCGGTTGAT AATCAGAAAA GCCCC 25

( 2 ) INFORMATION FOR SEQ ID NO:13:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( v i ) ORIGINAL SOURCE:
    ( A ) ORGANISM: synthetic ( x i ) SEQUENCE DESCRIPTION: SEQ ID NO:13:

CCCGGTTGAT AATCAGAAAA GCCCCCCCGC ACCGATCGCC GCGGGCCTCT TCGCTATTAC 60

GCCAGCTGGC GAAAGGGGGA 80

( 2 ) INFORMATION FOR SEQ ID NO:14:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( v i ) ORIGINAL SOURCE:
    ( A ) ORGANISM: synthetic ( x i ) SEQUENCE DESCRIPTION: SEQ ID NO:14:

CCCGGTTGAT AATCAGAAAA GCCCCCCCGC ACCGATCGCC 40

( 2 ) INFORMATION FOR SEQ ID NO:15:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal

5,679,512

( v i ) ORIGINAL SOURCE:
                    ( A ) ORGANISM: synthetic ( x i ) SEQUENCE DESCRIPTION: SEQ ID NO:15:

GCGGGCCTCT TCGCTATTAC GCCAGCTGGC GAAAGGGGGA                    40

( 2 ) INFORMATION FOR SEQ ID NO:16:

( i ) SEQUENCE CHARACTERISTICS:
                    ( A ) LENGTH: 5 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( v i ) ORIGINAL SOURCE:
                    ( A ) ORGANISM: synthetic ( x i ) SEQUENCE DESCRIPTION: SEQ ID NO:16:

CCCGC                    5

( 2 ) INFORMATION FOR SEQ ID NO:17:

( i ) SEQUENCE CHARACTERISTICS:
                    ( A ) LENGTH: 10 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( v i ) ORIGINAL SOURCE:
                    ( A ) ORGANISM: synthetic ( x i ) SEQUENCE DESCRIPTION: SEQ ID NO:17:

ACCGATCGCC                    10

( 2 ) INFORMATION FOR SEQ ID NO:18:

( i ) SEQUENCE CHARACTERISTICS:
                    ( A ) LENGTH: 25 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( v i ) ORIGINAL SOURCE:
                    ( A ) ORGANISM: synthetic ( x i ) SEQUENCE DESCRIPTION: SEQ ID NO:18:

CCCGGTTGAT AATCAGAAAA GCCCC                    25

( 2 ) INFORMATION FOR SEQ ID NO:19:

( i ) SEQUENCE CHARACTERISTICS:
           ( A ) LENGTH: 80 base pairs
           ( B ) TYPE: nucleic acid
           ( C ) STRANDEDNESS: single
           ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( v i ) ORIGINAL SOURCE:
           ( A ) ORGANISM: synthetic ( x i ) SEQUENCE DESCRIPTION: SEQ ID NO:19:

```
CCCGGTTGAT AATCAGAAAA GCCCCCCCGC ACCGATCGCC GCGGGCCTCT TCGCTATTAC        60

GCCAGCTGGC GAAAGGGGA                                                    80
```

( 2 ) INFORMATION FOR SEQ ID NO:20:

( i ) SEQUENCE CHARACTERISTICS:
           ( A ) LENGTH: 25 base pairs
           ( B ) TYPE: nucleic acid
           ( C ) STRANDEDNESS: single
           ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( v i ) ORIGINAL SOURCE:
           ( A ) ORGANISM: synthetic ( x i ) SEQUENCE DESCRIPTION: SEQ ID NO:20:

```
CAAAACAGCG GAAGAGCGTG AAATC                                             25
```

( 2 ) INFORMATION FOR SEQ ID NO:21:

( i ) SEQUENCE CHARACTERISTICS:
           ( A ) LENGTH: 80 base pairs
           ( B ) TYPE: nucleic acid
           ( C ) STRANDEDNESS: single
           ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( v i ) ORIGINAL SOURCE:
           ( A ) ORGANISM: synthetic ( x i ) SEQUENCE DESCRIPTION: SEQ ID NO:21:

```
CAAAACAGCG GAAGAGCGTG AAATCGGCCC TGACAGTGTG GGGCCGCGGT ACGCTGATCA        60

AAGATCCGTG CAACAAATGT                                                   80
```

( 2 ) INFORMATION FOR SEQ ID NO:22:

( i ) SEQUENCE CHARACTERISTICS:

(A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: internal (vi) ORIGINAL SOURCE:
        (A) ORGANISM: synthetic (xi) SEQUENCE DESCRIPTION: SEQ ID NO:22:

TAGCCCTTGT CGAACCGCAT ACCCT                                                         25

(2) INFORMATION FOR SEQ ID NO:23:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: internal (vi) ORIGINAL SOURCE:
        (A) ORGANISM: synthetic (xi) SEQUENCE DESCRIPTION: SEQ ID NO:23:

TAGCCCTTGT CGAACCGCAT ACCCTGTGTG TCCATATGGA CACACCATCG TTGGTGATCG                    60

TGGGGGCACC                                                                          70